United States Patent
An et al.

(10) Patent No.: US 12,118,716 B2
(45) Date of Patent: Oct. 15, 2024

(54) OPHTHALMOLOGIC INFORMATION PROCESSING APPARATUS, OPHTHALMOLOGIC IMAGING APPARATUS, OPHTHALMOLOGIC INFORMATION PROCESSING METHOD, AND RECORDING MEDIUM

(71) Applicant: Topcon Corporation, Tokyo (JP)

(72) Inventors: Guangzhou An, Tokyo (JP); Masahiro Akiba, Wako (JP); Tsutomu Kikawa, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 725 days.

(21) Appl. No.: 17/306,957

(22) Filed: May 4, 2021

(65) Prior Publication Data
US 2021/0272283 A1    Sep. 2, 2021

Related U.S. Application Data

(63) Continuation of application No. PCT/JP2019/048368, filed on Dec. 11, 2019.

(30) Foreign Application Priority Data

Dec. 26, 2018 (JP) ................. 2018-243153

(51) Int. Cl.
*G06T 7/00* (2017.01)
*A61B 3/12* (2006.01)
*A61B 3/14* (2006.01)

(52) U.S. Cl.
CPC .............. *G06T 7/0012* (2013.01); *A61B 3/12* (2013.01); *A61B 3/14* (2013.01); *G06T 2207/20081* (2013.01); *G06T 2207/30041* (2013.01)

(58) Field of Classification Search
CPC ......... G06T 7/0012; G06T 2207/20081; G06T 2207/30041; G06T 2207/20084;
(Continued)

(56) References Cited

U.S. PATENT DOCUMENTS

2011/0044543 A1* 2/2011 Nakamura ........... G06V 20/588
382/190
2012/0070049 A1* 3/2012 Iwase ...................... G06T 7/62
382/128
(Continued)

FOREIGN PATENT DOCUMENTS

JP    2004-301729 A    10/2004
JP    2007-89976 A    4/2007
(Continued)

OTHER PUBLICATIONS

International Search Report and Written Opinion mailed on Mar. 3, 2020, received for PCT Application No. PCT/JP2019/048368, Filed on Dec. 11, 2019, 9 pages including English Translation.
(Continued)

*Primary Examiner* — Mohammed A Hasan
(74) *Attorney, Agent, or Firm* — XSENSUS LLP

(57) ABSTRACT

An ophthalmologic information processing apparatus includes an acquisition unit and a determination unit. The acquisition unit is configured to acquire a captured image of a subject's eye. The determination unit is configured to determine whether or not the captured image acquired by the acquisition unit is an analysis error image including a predetermined analysis error factor.

23 Claims, 17 Drawing Sheets

(58) Field of Classification Search
CPC ....... G06T 7/0002; G06T 7/0016; G06T 7/11; G06T 7/12; G06T 7/136; G06T 2200/04; G06T 2207/10101; G06T 2207/30168; A61B 3/12; A61B 3/14; A61B 3/1225; A61B 3/102
USPC .......................................................... 351/246
See application file for complete search history.

(56) References Cited

U.S. PATENT DOCUMENTS

| | | | | |
|---|---|---|---|---|
| 2012/0218517 A1* | 8/2012 | Imamura | ............. | A61B 3/1025 382/128 |
| 2013/0093995 A1* | 4/2013 | Suehira | ................. | A61B 3/102 351/246 |
| 2013/0145183 A1* | 6/2013 | Wada | ..................... | G06Q 50/06 713/300 |
| 2018/0153401 A1 | 6/2018 | Strozyk et al. | | |

FOREIGN PATENT DOCUMENTS

| | | |
|---|---|---|
| JP | 2010-110656 A | 5/2010 |
| JP | 2011-97998 A | 5/2011 |
| JP | 2012-28992 A | 2/2012 |
| JP | 2016-51205 A | 4/2016 |
| JP | 2018-89305 A | 6/2018 |

OTHER PUBLICATIONS

Japanese Notice of Reasons for Refusal issued May 24, 2022, in Japanese Application No. 2018-243153.

Office Action issued on Aug. 23, 2022, in corresponding Japanese patent Application No. 2018-243153, 8 pages.

* cited by examiner

OPHTHALMOLOGIC INFORMATION PROCESSING APPARATUS, OPHTHALMOLOGIC IMAGING APPARATUS, OPHTHALMOLOGIC INFORMATION PROCESSING METHOD, AND RECORDING MEDIUM

CROSS-REFERENCE TO RELATED APPLICATIONS

The present application is a continuation application of International Patent Application No. PCT/JP2019/048368, filed Dec. 11, 2019, which claims priority to Japanese Patent Application No. 2018-243153, filed Dec. 26, 2018. The contents of these applications are incorporated herein by reference in their entirety.

FIELD

The disclosure relates to an ophthalmologic information processing apparatus, an ophthalmologic imaging apparatus, an ophthalmologic information processing method, and a recording medium.

BACKGROUND

In recent years, attention has been drawn to optical coherence tomography (OCT) which is used to measure the morphology of an object to be measured or to image using light beam emitted from a laser light source or the like. Since OCT does not have invasiveness to human body as X-ray CT (Computed Tomography) does, development of application of OCT in medical field and biology field is particularly expected. For example, in the ophthalmologic field, apparatuses for forming images of the fundus or the cornea have been in practical use. Such apparatuses using OCT (OCT apparatuses) can be used to observe a variety of sites (a fundus, or an anterior segment) of a subject's eye. In addition, because of the ability to acquire high precision images, the OCT apparatuses are applied to the diagnosis of various eye diseases.

Measurement results such as images obtained by OCT and their analysis results are useful for early detection and early diagnosis of lifestyle-related diseases and eye diseases such as glaucoma. Thereby, for example, the inspection using the OCT apparatus is performed in medical checkup (health check) or the like. However, due to the influence of the time required for OCT measurement and the skill of the operator of the apparatus, mixing of measurement results that are not suitable for analysis may be found after the fact, and the operating efficiency such as medical checkup may decrease due to re-measurement or the like.

For example, Japanese Unexamined Patent Application Publication No. 2010-110656 discloses an apparatus capable of determining the continuity of the volume data of the tomographic image of the subject's eye and performing re-photographing according to an instruction from the operator referring to the determination result displayed on the display unit.

For example, Japanese Unexamined Patent Application Publication No. 2011-97998 discloses an ophthalmologic imaging apparatus that displays an acquired image of the subject's eye on a display monitor and shifts to a state in which re-photographing can be performed when an examiner who sees the displayed image gives an instruction via an operation unit.

SUMMARY

One aspect of some embodiments is an ophthalmologic information processing apparatus, including: an acquisition unit configured to acquire a captured image of a subject's eye; and a determination unit configured to determine whether or not the captured image acquired by the acquisition unit is an analysis error image including a predetermined analysis error factor.

Another aspect of some embodiments is an ophthalmologic imaging apparatus including an imaging unit configured to acquire the captured image by imaging the subject's eye; and the ophthalmologic information processing apparatus described above.

Still another aspect of some embodiments is an ophthalmologic information processing method including an acquisition step of acquiring a captured image of a subject's eye; and a determination step of determining whether or not the captured image acquired in the acquisition step is an analysis error image including a predetermined analysis error factor.

Still another aspect of some embodiments is a computer readable non-transitory recording medium in which a program for causing a computer to execute each step of the ophthalmologic information processing method described above is recorded.

DETAILED DESCRIPTION

Figure 1:
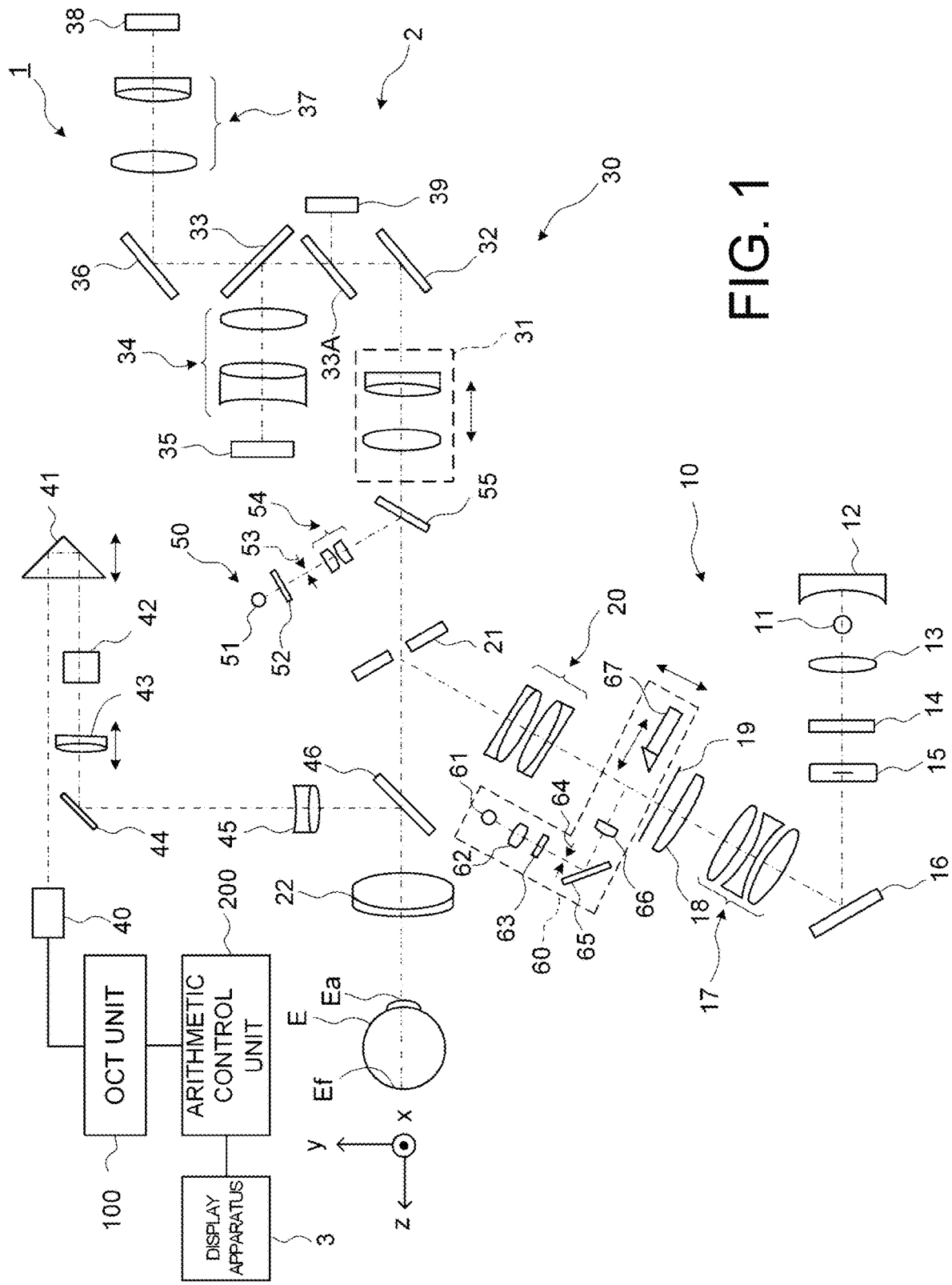
FIG. 1 is a schematic diagram illustrating an example of the configuration of the ophthalmologic imaging apparatus according to embodiments.

In general, the criteria for judging the quality of a captured image such as an OCT image of the subject's eye acquired by an ophthalmologic imaging apparatus are different from the criteria for judging whether or not the captured image is suitable for analysis for early detection and diagnosis of eye diseases. In other words, there are cases where a captured image that is judged to be a good image is not suitable for analysis, and cases where a captured image that is judged not to be a good image is suitable for analysis. This difference in judgment criteria may result in unnecessary re-measurement work.

According to some embodiments of the present invention, a new technique for efficiently acquiring an image of a subject's eye suitable for analysis can be provided.

Referring now to the drawings, exemplary embodiments of an ophthalmologic information processing apparatus, an ophthalmologic imaging apparatus, an ophthalmologic information processing method, a program, and a recording medium according to the present invention are described below. Any of the contents of the documents cited in the present specification and arbitrary known techniques may be applied to the embodiments below.

The ophthalmologic information processing apparatus acquires a captured image obtained by imaging (photographing) a subject's eye, and determines whether or not the acquired captured image is an analysis error image including a predetermined analysis error factor before performing predetermined analysis processing on the captured image. The analysis error image is an image highly likely to result in an analysis error even if the predetermined analysis processing is performed in the future, or an image highly likely to reduce the reliability of the results of the predetermined analysis processing. This allows to determine the suitability of analysis for the acquired captured image and to determine whether or not re-imaging (re-measurement) is necessary, immediately after imaging the subject's eye. Thereby, images suitable for analysis can be efficiently acquired. Further, this allows to determine the suitability of analysis for the captured image based on criteria for determining whether or not it is suitable for analysis, without using the quality of the captured image as the criteria. Thereby, the occurrence of unnecessary re-imaging work can be suppressed.

An ophthalmologic information processing method according to the embodiments includes one or more steps for realizing the processing executed by a processor (computer) in the ophthalmologic information processing apparatus according to the embodiments. A program according to the embodiments causes the processor to execute each step of the ophthalmologic information processing method according to the embodiments. A recording medium according to the embodiments is a computer readable non-transitory recording medium (storage medium) on which the program according to the embodiments is recorded.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

In the following, a case where the captured image of the subject's eye is an OCT image formed based on OCT data obtained by performing OCT on the subject's eye will be described. However, the captured image of the subject's eye according to the embodiments may be an image acquired by an ophthalmologic imaging apparatus such as a fundus camera, a scanning laser ophthalmoscope (SLO), a slit lamp ophthalmoscope, or a surgical microscope.

In the following, a case where the captured image of the subject's eye according to the embodiments is a fundus image will be described. However, the captured image of the subject's eye according to the embodiments may be an anterior segment image.

In this specification, an image acquired using OCT may be collectively referred to as an "OCT image". Also, the measurement operation for forming OCT images may be referred to as OCT measurement.

The ophthalmologic imaging apparatus according to the embodiments realizes the function of the ophthalmologic information processing apparatus according to the embodiments. The ophthalmologic imaging apparatus according to the embodiments includes at least one of an OCT apparatus capable of performing OCT measurement, a fundus camera, a scanning laser ophthalmoscope, a slit lamp ophthalmoscope, a surgical microscope, and the like. The ophthalmologic imaging apparatus according to some embodiments further includes at least one of an ophthalmologic measuring apparatus and an ophthalmologic therapy apparatus. The ophthalmologic measuring apparatus according to some embodiments includes at least one of an eye refractivity examination apparatus, a tonometer, a specular microscope, a wave-front analyzer, a perimeter, and a microperimeter. The ophthalmologic therapy according to some embodiments includes at least one of a laser therapy apparatus, a surgical apparatus and a surgical microscope.

First Embodiment

The ophthalmologic imaging apparatus according to a first embodiment includes an OCT apparatus and a fundus camera. Alternatively, the configuration according to the following embodiments may be applied to a single-functional OCT apparatus.

Hereinafter, an ophthalmologic imaging apparatus capable of performing OCT measurement on a fundus of the subject's eye will be described as an example. However, the ophthalmologic imaging apparatus according to the embodiments may be capable of performing OCT measurement on an anterior segment of the subject's eye. In some embodiments, a measurement site of the OCT measurement and/or a range of the OCT measurement are/is changed by moving a lens for changing focal position of measurement light. In some embodiments, the ophthalmologic imaging apparatus has a configuration capable of performing OCT measurement on the fundus, OCT measurement on the anterior segment, and OCT measurement on the whole eyeball including the fundus and anterior segment, by adding one or more attachments (objective lens, front lens, etc.). In some embodiments, in the ophthalmologic imaging apparatus for measuring fundus, OCT measurement is performed on the anterior segment, by making the measurement light incident on the subject's eye, the measurement light having been converted into a parallel light flux by arranging a front lens between the objective lens and the subject's eye.

<Configuration>

[Optical System]

As shown in FIG. 1, the ophthalmologic imaging apparatus 1 includes a fundus camera unit 2, an OCT unit 100, and an arithmetic control unit 200. The fundus camera unit 2 is provided with an optical system and a mechanism for acquiring front images of a subject's eye E. The OCT unit 100 is provided with a part of an optical system and a mechanism for performing OCT. Another part of the optical system and the mechanism for performing OCT are provided in the fundus camera unit 2. The arithmetic control unit 200 includes one or more processors for performing various kinds of arithmetic processing and control processing. In addition to these elements, an arbitrary element or a unit, such as a member (chin rest, forehead pad, etc.) for supporting a face of the subject, a lens unit (for example, an attachment for an anterior segment OCT) for switching the target site of OCT, and the like, may be provided in the ophthalmologic imaging apparatus 1. In some embodiments, the lens unit is configured to be manually inserted and removed between the subject's eye E and an objective lens 22 described later. In some embodiments, the lens unit is configured to be automatically inserted and removed between the subject's eye E and the objective lens 22 described later, under the control of the controller 210 described later.

[Fundus Camera Unit]

The fundus camera unit 2 is provided with an optical system for imaging (photographing) a fundus Ef of the subject's eye E. An image (called fundus image, fundus photograph, etc.) of the fundus Ef to be obtained is a front image such as an observation image, a captured image. The observation image is obtained by moving image shooting using near infrared light. The captured image may be a still image using flash light. Furthermore, the fundus camera unit 2 can obtain the front image (anterior segment image) by photographing (imaging) an anterior segment Ea of the subject's eye E.

The fundus camera unit 2 includes an illumination optical system 10 and an imaging (photographing) optical system 30. The illumination optical system 10 projects illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

Light (observation illumination light) emitted from the observation light source 11 of the illumination optical system 10 is reflected by a reflective mirror 12 having a curved reflective surface, and becomes near-infrared light after being transmitted through a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of a hole part) of a perforated mirror 21, is transmitted through a dichroic mirror 46, and is refracted by an objective lens 22, thereby illuminating the subject's eye E (fundus Ef or anterior segment Ea). Returning light of the observation illumination light reflected from the subject's eye E is refracted by the objective lens 22, is transmitted through the dichroic mirror 46, passes through the hole part formed in the center region of the perforated mirror 21, is transmitted through a dichroic mirror 55. The returning light transmitted through the dichroic mirror 55 travels through an imaging focusing lens 31 and is reflected by a mirror 32. Further, this returning light is transmitted through a half mirror 33A, is reflected by a dichroic mirror 33, and forms an image on the light receiving surface of an image sensor 35 by a condenser lens 34. The image sensor 35 detects the returning light at a predetermined frame rate. It should be noted that the focus of the imaging optical system 30 is adjusted so as to coincide with the fundus Ef or the anterior segment Ea.

Light (imaging illumination light) emitted from the imaging light source 15 is projected onto the fundus Ef via the same route as that of the observation illumination light. Returning light of the imaging illumination light from the subject's eye E is guided to the dichroic mirror 33 via the same route as that of the observation illumination light, is transmitted through the dichroic mirror 33, is reflected by a mirror 36, and forms an image on the light receiving surface of the image sensor 38 by a condenser lens 37.

A liquid crystal display (LCD) 39 displays a fixation target and a visual target used for visual acuity measurement. Part of light output from the LCD 39 is reflected by the half mirror 33A, is reflected by the mirror 32, travels through the imaging focusing lens 31 and the dichroic mirror 55, and passes through the hole part of the perforated mirror 21. The light flux (beam) having passed through the hole part of the perforated mirror 21 is transmitted through the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position include a fixation position for acquiring an image centered at a macula, a fixation position for acquiring an image centered at an optic disc, a fixation position for acquiring an image centered at a fundus center between the macula and the optic disc, a fixation position for acquiring an image of a site (fundus peripheral part) far away from the macula, and the like. The ophthalmologic imaging apparatus 1 according to some embodiments includes GUI (Graphical User Interface) and the like for designating at least one of such fixation positions. The ophthalmologic imaging apparatus 1 according to some embodiments includes GUI etc. for manually moving the fixation position (display position of the fixation target).

The configuration for presenting the movable fixation target to the subject's eye E is not limited to the display device such LCD or the like. For example, the movable fixation target can be generated by selectively turning on a plurality of light sources of a light source array (light emitting diode (LED) array or the like). Alternatively, the movable fixation target can be generated using one or more movable light sources.

Further, the ophthalmologic imaging apparatus 1 may be provided with one or more external fixation light sources. One of the one or more external fixation light sources can project fixation light onto a fellow eye of the subject's eye E. A projected position of the fixation light on the fellow eye can be changed. By changing the projected position of the fixation light on the fellow eye, the fixation position of the subject's eye E can be changed. The fixation position projected by the external fixation light source(s) may be the same as the fixation position of the subject's eye E using the LCD 39. For example, the movable fixation target can be generated by selectively turning on the plurality of external fixation light sources. Alternatively, the movable fixation target can be generated using one or more movable external fixation light sources.

The alignment optical system 50 generates an alignment indicator for alignment of the optical system with respect to the subject's eye E. Alignment light emitted from an LED 51 travels through the diaphragms 52 and 53 and the relay lens 54, is reflected by the dichroic mirror 55, and passes through the hole part of the perforated mirror 21. The alignment light having passed through the hole part of the perforated mirror 21 is transmitted through the dichroic mirror 46, and is projected onto the subject's eye E by the objective lens 22. Corneal reflection light of the alignment light is guided to the image sensor 35 through the same route as the returning light of the observation illumination light. Manual alignment or automatic alignment can be performed based on the received light image (alignment indicator image) thereof.

The focus optical system 60 generates a split indicator for adjusting the focus with respect to the subject's eye E. The focus optical system 60 is movable along an optical path (illumination optical path) of the illumination optical system 10 in conjunction with the movement of the imaging focusing lens 31 along an optical path (imaging optical path) of the imaging optical system 30. The reflection rod 67 can be inserted and removed into and from the illumination optical path. To perform focus adjustment, the reflective surface of the reflection rod 67 is arranged in a slanted position on the illumination optical path. Focus light emitted from an LED 61 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the perforated mirror 21, is transmitted through the dichroic mirror 46, and is refracted by the objective lens 22, thereby being projected onto the fundus Ef. Fundus reflection light of the focus light is guided to the image sensor 35 through the same route as the corneal reflection light of the alignment light. Manual focus or automatic focus can be performed based on the received light image (split indicator image) thereof.

The dichroic mirror 46 combines an optical path for imaging and an optical path for OCT (optical path of the interference optical system). The dichroic mirror 46 reflects light of wavelength band used in OCT, and transmits light for fundus imaging. The optical path for OCT (optical path of measurement light) is provided with, in order from the OCT unit 100 side to the dichroic mirror 46 side, a collimator lens unit 40, an optical path length changing unit 41, an optical scanner 42, an OCT focusing lens 43, a mirror 44, and a relay lens 45.

The optical path length changing unit 41 is movable in directions indicated by the arrow in FIG. 1, thereby changing the length of the optical path for OCT. This change in the optical path length is used for correcting the optical path length according to the axial length, adjusting the interference state, or the like. The optical path length changing unit 41 includes a corner cube and a mechanism for moving the corner cube.

The optical scanner 42 is disposed at a position optically conjugate with the pupil of the subject's eye E. The optical scanner 42 deflects the measurement light LS traveling along the OCT optical path. The optical scanner 42 can deflect the measurement light LS in a one-dimensionally or two-dimensional manner.

In case that the optical scanner deflects the measurement light LS in a one-dimensionally manner, the optical scanner 42 includes a galvano scanner capable of deflecting the measurement light LS within a predetermined deflection angle range in a predetermined deflection direction. In case that the optical scanner deflects the measurement light LS in a two-dimensionally manner, the optical scanner 42 includes a first galvano scanner and a second galvano scanner. The first galvano scanner deflects the measurement light LS so as to scan an imaging site (fundus Ef or the anterior segment Ea) in a horizontal direction orthogonal to the optical axis of the interference optical system (OCT optical system). The second galvano scanner deflects the measurement light LS deflected by the first galvano scanner so as to scan the imaging site in a vertical direction orthogonal to the optical axis of the interference optical system. Examples of scan mode with the measurement light LS performed by the optical scanner 42 include horizontal scan, vertical scan, cross scan, radial scan, circle scan, concentric scan, helical (spiral) scan, and the like.

The OCT focusing lens 43 is moved along the optical path of the measurement light LS in order to perform focus adjustment of the optical system for OCT. The OCT focusing lens 43 can move within a moving range. The moving range includes a first lens position for placing the focal position of the measurement light LS at the fundus Ef or near the fundus Ef of the subject's eye E and a second lens position for making the measurement light LS projected onto the subject's eye E a parallel light beam. The movement of the imaging focusing lens 31, the movement of the focus optical system 60, and the movement of the OCT focusing lens 43 can be controlled in conjunction with each other.

[Oct Unit]

Figure 2:
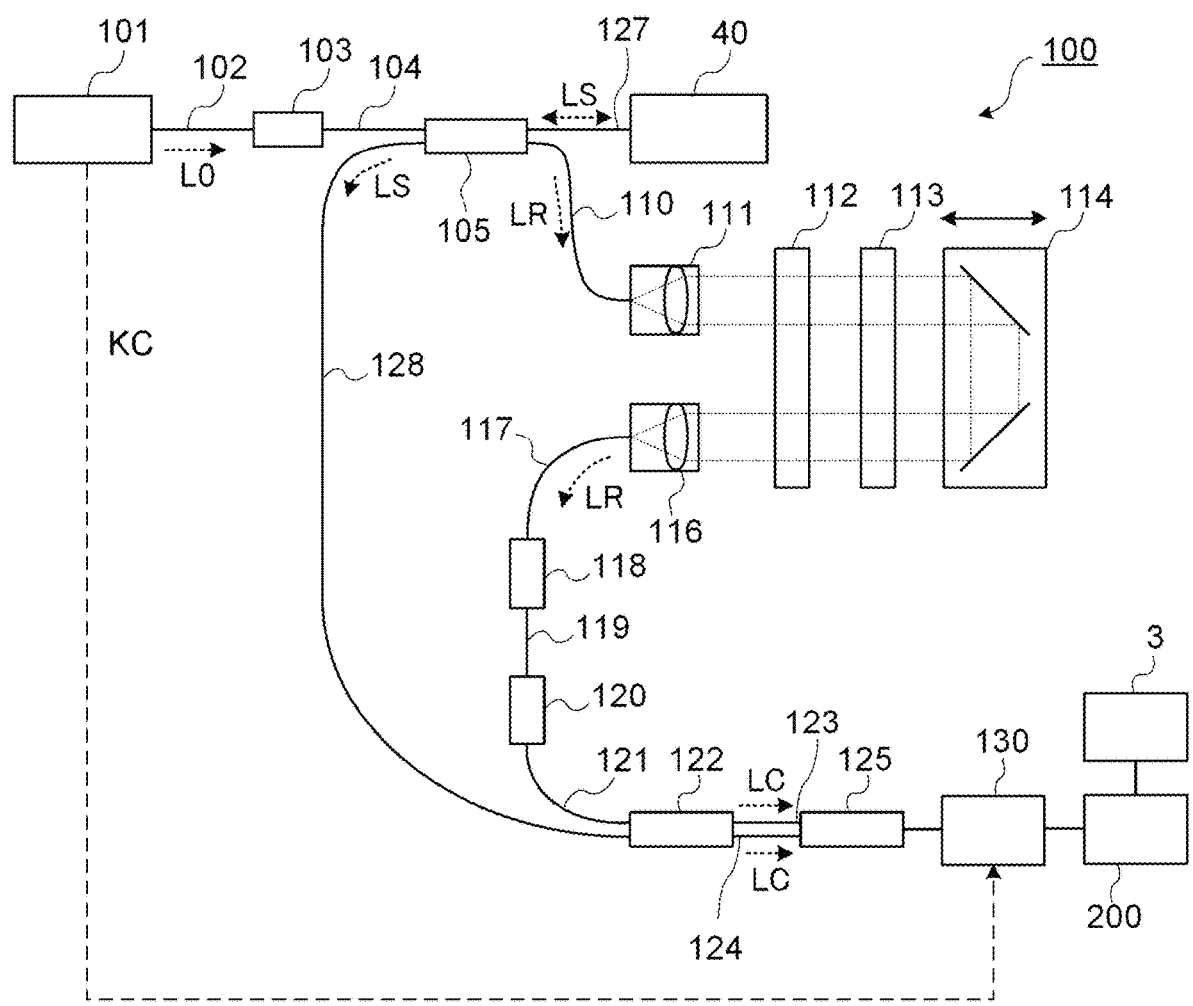
FIG. 2 is a schematic diagram illustrating an example of the configuration of the ophthalmologic imaging apparatus according to the embodiments.

An example of the configuration of the OCT unit 100 is shown in FIG. 2. The OCT unit 100 is provided with an optical system for acquiring OCT images of the subject's eye E. The optical system includes an interference optical system that splits light from a wavelength sweeping type (i.e., a wavelength scanning type) light source into measurement light and reference light, makes the measurement light returning from the subject's eye E and the reference light having traveled through the reference optical path interfere with each other to generate interference light, and detects the interference light. The detection result of the interference light obtained by the interference optical system (i.e., the detection signal) is an interference signal indicating the spectrum of the interference light, and is sent to the arithmetic control unit 200.

Like swept source type ophthalmologic apparatuses commonly used, the light source unit 101 includes a wavelength sweeping type (i.e., a wavelength scanning type) light source capable of sweeping (scanning) the wavelengths of emitted light. The wavelength sweeping type light source includes a laser light source that includes a resonator. The light source unit 101 temporally changes the output wavelengths within the near-infrared wavelength bands that cannot be visually recognized with human eyes.

The light L0 output from the light source unit 101 is guided to the polarization controller 103 by the optical fiber 102, and the polarization state of the light L0 is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110. The reference light LR is converted into a parallel light beam by the collimator 111. Then, the reference light LR is guided to the optical path length changing unit 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The optical path length changing unit 114 includes, for example, a corner cube and a movement mechanism for moving the corner cube and can move the corner cube in the incident direction of the reference light LR using the movement mechanism. Thereby, the optical path length of the reference light LR is changed.

The reference light LR that has traveled through the optical path length changing unit 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through an optical fiber 127, and is made into a parallel light beam by the collimator lens unit 40. The measurement light LS made into the parallel light beam travels through the optical path length changing unit 41, the optical scanner 42, the OCT focusing lens 43, the mirror 44, and the relay lens 45. The measurement light LS having traveled through the relay lens 45 is reflected by the dichroic mirror 46, is refracted by the objective lens 22, and is irradiated onto the subject's eye E. The measurement light LS is scattered and reflected at various depth positions of the subject's eye E. Returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC is guided to a detector 125 through optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the data acquisition system (DAQ) 130. A clock KC is supplied from the light source unit 101 to the DAQ 130. The clock KC is generated in the light source unit 101 in synchronization with the output timing of each wavelength sweeping (scanning) within a predetermined wavelength range performed by the wavelength sweeping type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs sampling of the detection result obtained by the detector 125 based on the clock KC. The DAQ 130 sends the result of the sampling of the detection result obtained by the detector 125 to the arithmetic control unit 200. For example, the arithmetic control unit 200 performs the Fourier transform etc. on the spectral distribution based on the detection result obtained by the detector 125 for each series of wavelength scanning (i.e., for each A-line). With this, the reflection intensity profile for each A-line is formed. In addition, the arithmetic control unit 200 forms image data by applying imaging processing to the reflection intensity profiles for the respective A-lines.

The configuration shown in FIG. 1 and FIG. 2 includes both the optical path length changing unit 41 that changes the length of the optical path of the measurement light LS (i.e., measurement optical path or measurement arm) and the optical path length changing unit 114 that changes the length of the optical path of the reference light LR (i.e., reference optical path or reference arm). However, any one of the optical path length changing units 41 and 114 may be provided. The difference between the measurement optical path length and the reference optical path length can be changed by using other optical members.

[Arithmetic Control Unit]

The arithmetic control unit 200 analyzes the detection signals fed from the DAQ 130 to form an OCT image of the subject's eye E. The arithmetic processing therefor is performed in the same manner as in the conventional swept-source-type OCT apparatus.

In addition, the arithmetic control unit 200 controls each part of the fundus camera unit 2, the display apparatus 3, and the OCT unit 100.

Also, as the control of the fundus camera unit 2, the arithmetic control unit 200 performs following controls: the operation control of the observation light source 11, the operation control of the imaging light source 15 and the operation control of the LEDs 51 and 61; the operation control of the LCD 39; the movement control of the imaging focusing lens 31; the movement control of the OCT focusing lens 43; the movement control of the reflection rod 67; the movement control of the focus optical system 60; the movement control of the optical path length changing unit 41; the operation control of the optical scanner 42, and the like.

As the control of the display apparatus 3, the arithmetic control unit 200 controls the display apparatus 3 to display the OCT image of the subject's eye E.

As the control of the OCT unit 100, the arithmetic control unit 200 controls: the operation of the light source unit 101; the operation of the optical path length changing unit 114; the operations of the attenuator 120; the operation of the polarization controllers 103 and 118; the operation of the detector 125; the operation of the DAQ 130; and the like.

As in the conventional computer, the arithmetic control unit 200 includes a microprocessor, RAM, ROM, hard disk drive, and communication interface, for example. A storage device such as the hard disk drive stores a computer program for controlling the ophthalmologic imaging apparatus 1. The arithmetic control unit 200 may include various kinds of circuitry such as a circuit board for forming OCT images. In addition, the arithmetic control unit 200 may include an operation device (or an input device) such as a keyboard and a mouse, and a display device such as an LCD.

The fundus camera unit 2, the display apparatus 3, the OCT unit 100, and the arithmetic control unit 200 may be integrally provided (i.e., in a single housing), or they may be separately provided in two or more housings.

[Control System]

Figure 3:
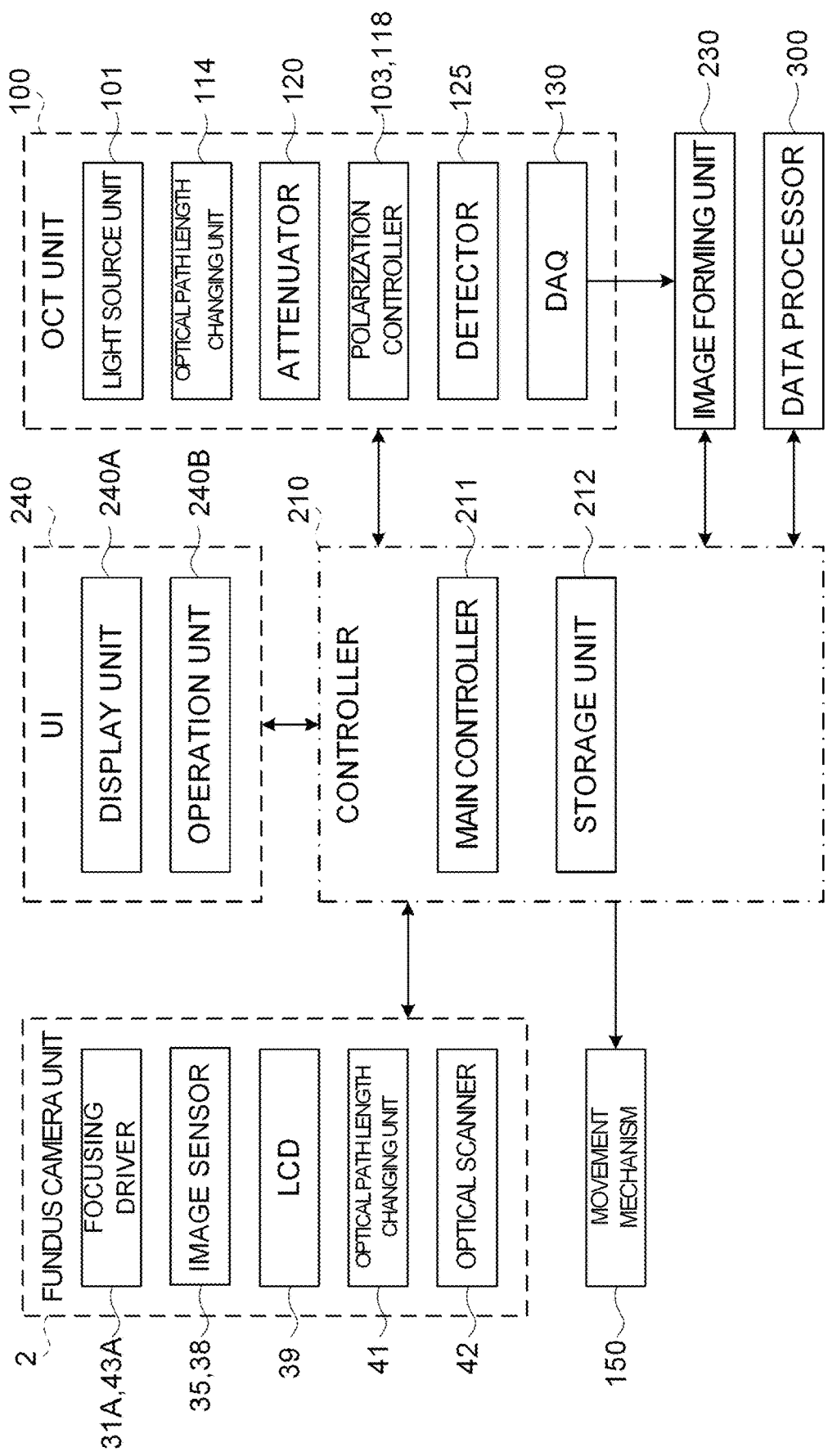
FIG. 3 is a schematic diagram illustrating an example of the configuration of the ophthalmologic imaging apparatus according to the embodiments.

FIG. 3 illustrates a configuration example of a control system of the ophthalmologic imaging apparatus 1. In FIG. 3, a part of the components included in the ophthalmologic imaging apparatus 1 is omitted.

The arithmetic control unit 200 includes a controller 210, and controls each part of the fundus camera unit 2, the display apparatus 3, and the OCT unit 100.

(Controller)

The controller 210 executes various controls. The controller 210 includes a main controller 211 and a storage unit 212.

(Main Controller)

The main controller 211 includes a processor and controls each part of the ophthalmologic imaging apparatus 1. For example, the main controller 211 controls components of the fundus camera unit 2 such as focusing drivers 31A and 43A, the image sensors 35 and 38, the LCD 39, the optical path length changing unit 41, the optical scanner 42, and the movement (movement mechanism 150) for moving the optical system. Further, the main controller 211 controls components of the OCT unit 100 such as the light source unit 101, the optical path length changing unit 114, the attenuator 120, the polarization controllers 103 and 118, the detector 125, and the DAQ 130.

For example, the main controller 211 controls the LCD 39 to display the fixation target at a position on the screen of the LCD 39 corresponding the fixation position set manually or automatically. Moreover, the main controller 211 can change the display position of the fixation target displayed on the LCD 39 (in a continuous manner or in a phased manner). Thereby, the fixation target can be moved (that is, the fixation position can be changed). The display position of the fixation target and movement mode of the fixation target are set manually or automatically. Manual setting is performed using GUI, for example. Automatic setting is performed by the data processor 300, for example.

The focusing driver 31A moves the imaging focusing lens 31 in the direction along the optical axis of the imaging optical system 30, and moves the focus optical system 60 in the direction along the optical axis of the illumination optical system 10. With this, the focus position of the imaging optical system 30 is changed. In some embodiments, the focusing driver 31A may include a dedicated mechanism for moving the imaging focusing lens 31 and a dedicated mechanism for moving the focus optical system 60. The focusing driver 31A is controlled when performing focus adjustment or the like.

The focusing driver 43A moves the OCT focusing lens 43 in the optical axis direction of the measurement optical path. Thereby, the focal position of the measurement light LS is changed. For example, the focus position of the measurement light LS can be arranged at the fundus Ef or near the fundus Ef by moving the OCT focusing lens 43 to the first lens position. For example, the focus position of the measurement light LS can be arranged at a far point position by moving the OCT focusing lens 43 to the second lens position. The focus position of the measurement light LS corresponds to the depth position (z position) of the beam waist of the measurement light LS.

The movement mechanism 150 three-dimensionally moves at least the fundus camera unit 2 (optical system), for example. In a typical example, the movement mechanism 150 includes a mechanism for moving at least the fundus camera unit 2 in the x direction (left-right direction), a mechanism for moving it in the y direction (up-down direction), and a mechanism for moving it in the z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main controller 211.

The control for the movement mechanism 150 is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement. In some embodiments, the movement mechanism 150 is configured to be controlled to change the optical path length of the reference light (that is, the difference of the optical path length between the optical path of the measurement light and the optical path of the reference light).

In the case of manual alignment, a user operates a user interface (UI) 240 described later to relatively move the optical system and subject's eye E so as to cancel the displacement of the subject's eye E with respect to the optical system. For example, the main controller 211 controls the movement mechanism 150 to relatively move the optical system and the subject's eye E by outputting a control signal corresponding to the operation content with respect to the user interface 240 to the movement mechanism 150.

In the case of automatic alignment, the main controller 211 controls the movement mechanism 150 to relatively move the optical system and the subject's eye E so as to cancel the displacement of the subject's eye E with respect to the optical system. In some embodiments, the main controller 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens 22, and it means the distance between the subject's eye E and the optical system when measuring (imaging) using the optical system.

The main controller 211 controls the fundus camera unit 2 etc. to control the fundus imaging (photography) and the anterior segment imaging. Further, the main controller 211 controls the fundus camera unit 2 and the OCT unit 100 etc. to control the OCT measurement. The main controller 211 is capable of performing a plurality of preliminary operations prior to OCT measurement. Examples of the preliminary operation include alignment, rough focus adjustment, polarization adjustment, and fine focus adjustment. The plurality of preliminary operations is performed in a predetermined order. In some embodiments, the plurality of preliminary operations is performed in an order described above.

It should be noted that the types and the orders of the preliminary operations are not so limited, and they may be optional. For example, the preliminary operations may further include small-pupil judgment. The small-pupil judgment is a preliminary operation to judge whether the pupil of the subject's eye E is small or not (whether the subject's eye E is microcoria or not). The small-pupil judgment may be performed between the rough focus adjustment and the optical path length difference adjustment. In some embodiments, the small-pupil judgment includes, for example, a series of processes as follows: acquiring a front image (anterior segment image) of the subject's eye E; specifying an image region corresponding to the pupil; calculating the size (e.g., diameter, circumference length) of the pupil region; judging whether the pupil of the subject's eye E is small or not based on the calculated size (threshold processing); and controlling the diaphragm 19 when judged that the pupil of the subject's eye E is small. In some embodiments, the calculation of the size of the pupil region includes processing of circularly or elliptically approximating the pupil region.

The rough focus adjustment is a kind of focus adjustment using the split indicator. The rough focus adjustment may be performed by determining the position of the imaging focusing lens 31 based on information, which is obtained by associating the eye refractive power acquired in advance with the position of the imaging focusing lens 31, and a measured value of the refractive power of the subject's eye E.

The fine focus adjustment is performed on the basis of interference sensitivity of OCT measurement. For example, the fine focus adjustment can be performed by: monitoring interference intensity (interference sensitivity) of interference signal acquired by performing OCT measurement of the subject's eye E; searching the position of the OCT focusing lens 43 so as to maximize the interference intensity; and moving the OCT focusing lens 43 to the searched position.

To perform the optical path length difference adjustment, the optical system is controlled so that a predetermined position on the subject's eye E is a reference position of a measurement range in the depth direction. The control is performed on at least one of the optical path length changing units 41 and 114. Thereby, the difference of the optical path length between the measurement optical path and the reference optical path is adjusted. By setting the reference position in the optical path length difference adjustment, OCT measurement can be performed with high accuracy over a desired measurement range in the depth direction simply by changing the wavelength sweep speed.

To perform the polarization adjustment, the polarization state of the reference light LR is adjusted for optimizing the interference efficiency between the measurement light LS and the reference light LR.

(Storage Unit)

The storage unit 212 stores various types of data. Examples of the data stored in the storage unit 212 include image data of an OCT image, image data of a fundus image, image data of an anterior segment image, and subject's eye information. The subject's eye information includes information on the subject such as patient ID and name, and information on the subject's eye such as identification information of the left eye/right eye.

In addition, the storage unit 212 stores various types of programs and data to run the ophthalmologic imaging apparatus 1.

The controller 210 can control an image forming unit 230 and a data processor 300.

(Image Forming Unit)

The image forming unit 230 forms an OCT image (image data) of the subject's eye E based on the sampling data obtained by sampling the detection signal from the detector 125 using the DAQ 130. Examples of the OCT image formed by the image forming unit 230 include an A-scan image, a B-scan image (tomographic image), a C-scan image, and the like. As with the conventional swept source OCT, the image formation process includes noise removal (noise reduction), filtering, dispersion compensation, fast Fourier transform (FFT), and the like. In the case of employing an OCT apparatus of another type, the image forming unit 230 performs known processing according to the type employed.

The image forming unit 230 includes, for example, the circuitry described above. It should be noted that "image data" and an "image" based on the image data may not be distinguished from each other in the present specification.

(Data Processor)

The data processor 300 processes data acquired through imaging of the subject's eye E or data acquired through OCT measurement. For example, the data processor 300 performs various kinds of image processing and various kinds of analysis processing on the image formed by the image forming unit 230. Specifically, the data processor 300 performs various types of image correction processing such as brightness correction. The data processor 300 performs various kinds of image processing and various kinds of analysis processing on images captured by the fundus camera unit 2 (e.g., fundus images, anterior segment images, etc.).

The data processor 300 performs known image processing such as interpolation for interpolating pixels in tomographic images to form image data of the three-dimensional image of the fundus Ef or the anterior segment Ea. Note that image data of the three-dimensional image means image data in which the positions of pixels are defined by a three-dimensional coordinate system. Examples of the image data of the three-dimensional image include image data defined by voxels three-dimensionally arranged. Such image data is referred to as volume data or voxel data. When displaying an image based on volume data, the data processor 300 performs rendering (volume rendering, maximum intensity projection (MIP), etc.) on the volume data, thereby forming image data of a pseudo three-dimensional image viewed from a particular line of sight. The pseudo three-dimensional image is displayed on the display device such as a display unit 240A.

The three-dimensional image data may be stack data of a plurality of tomographic images. The stack data is image data formed by three-dimensionally arranging tomographic images along a plurality of scan lines based on positional relationship of the scan lines. That is, the stack data is image data formed by representing tomographic images, which are originally defined in their respective two-dimensional coordinate systems, by a single three-dimensional coordinate system. That is, the stack data is image data formed by embedding tomographic images into a single three-dimensional space.

The data processor 300 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as the B-mode image or the C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

The data processor 300 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 300 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 300 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 300 is also included in the OCT image.

Further, the data processor 300 determines the focus state of the measurement light LS in fine focus adjustment control by analyzing the detection result of the interference light obtained by the OCT measurement. For example, the main controller 211 performs repetitive OCT measurements while controlling the focusing driver 43A according to a predetermined algorithm. The data processor 300 analyzes detection results of interference light LC repeatedly acquired by the OCT measurements to calculate predetermined evaluation values relating to image quality of OCT images. The data processor 300 determines whether the calculated evaluation value is equal to or less than a threshold. In some embodiments, the fine focus adjustment is continued until the calculated evaluation value becomes equal to or less than the threshold. That is, when the evaluation value is equal to or less than the threshold, it is determined that the focus state of the measurement light LS is appropriate. And the fine focus adjustment is continued until it is determined that the focus state of the measurement light LS is appropriate.

In some embodiments, the main controller 211 monitors the intensity of the interference signal (interference intensity, interference sensitivity) acquired sequentially while acquiring the interference signal by performing the repetitive OCT measurements described above. In addition, while performing this monitoring process, the OCT focusing lens 43 is moved to find the position of the OCT focusing lens 43 in which the interference intensity is maximized. With the fine focus adjustment thus performed, the OCT focusing lens 43 can be guided to the position where the interference intensity is optimized.

Further, the data processor 300 determines the polarization state of at least one of the measurement light LS and the reference light LR by analyzing the detection result of the interference light obtained by the OCT measurement. For example, the main controller 211 performs repetitive OCT measurements while controlling at least one of the polarization controllers 103 and 118 according to a predetermined algorithm. In some embodiments, the main controller 211 controls the attenuator 120 to change an attenuation of the reference light LR. The data processor 300 analyzes detection results of interference light LC repeatedly acquired by the OCT measurements to calculate predetermined evaluation values relating to image quality of OCT images. The data processor 300 determines whether the calculated evaluation value is equal to or less than a threshold. The threshold is set in advance. Polarization adjustment is continued until the evaluation value calculated becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 211 can monitor the interference intensity also in the polarization adjustment.

The data processor 300 according to the embodiments determines whether or not the image formed by the image forming unit 230 or the data processor 300 is an analysis error image including a predetermined analysis error factor. This allows to automatically determine whether or not re-imaging (re-acquisition, re-measurement) is necessary based on certain determination criteria.

Figure 4:
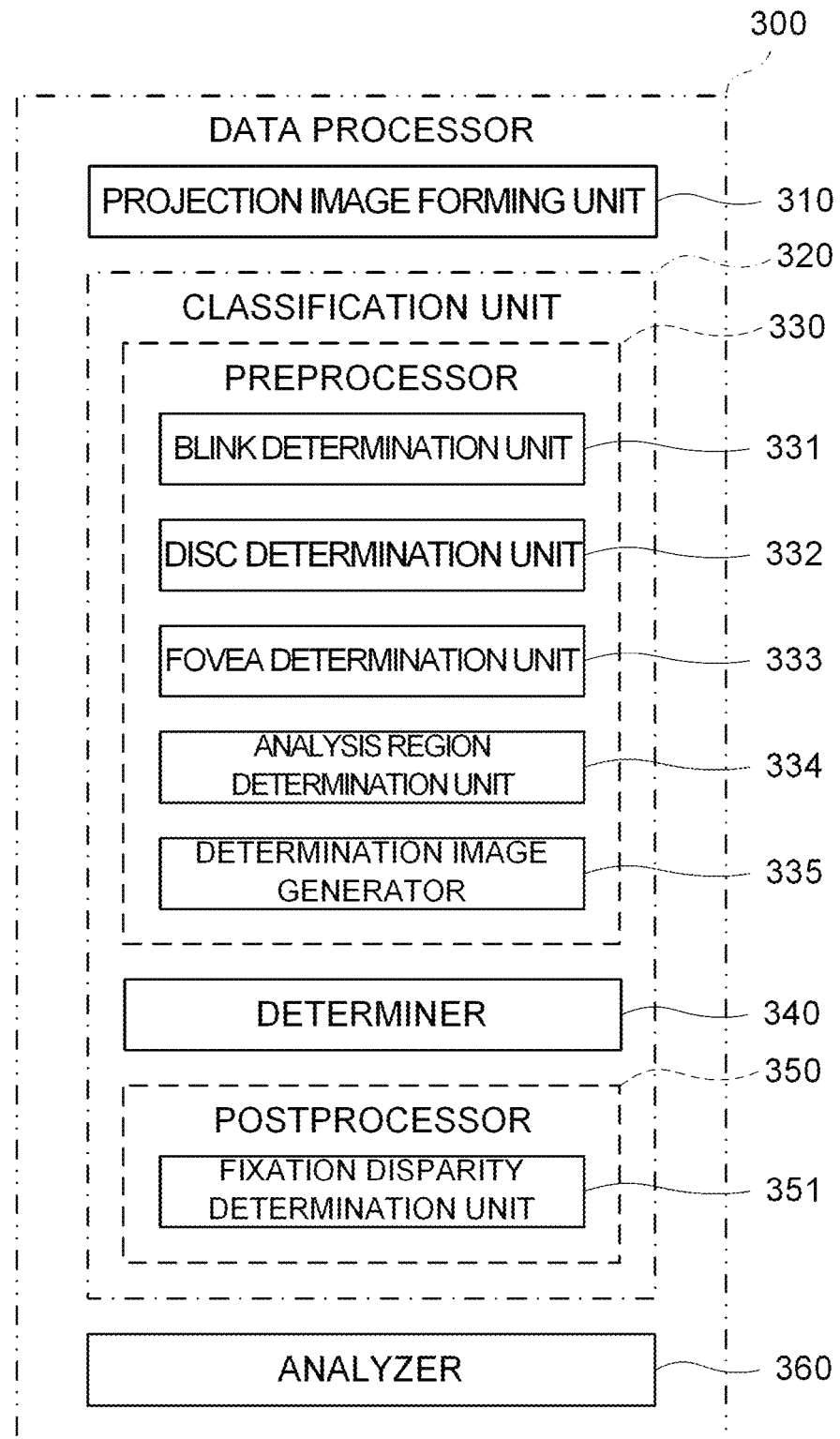
FIG. 4 is a schematic diagram illustrating an example of the configuration of the ophthalmologic imaging apparatus according to the embodiments.
Figure 5:
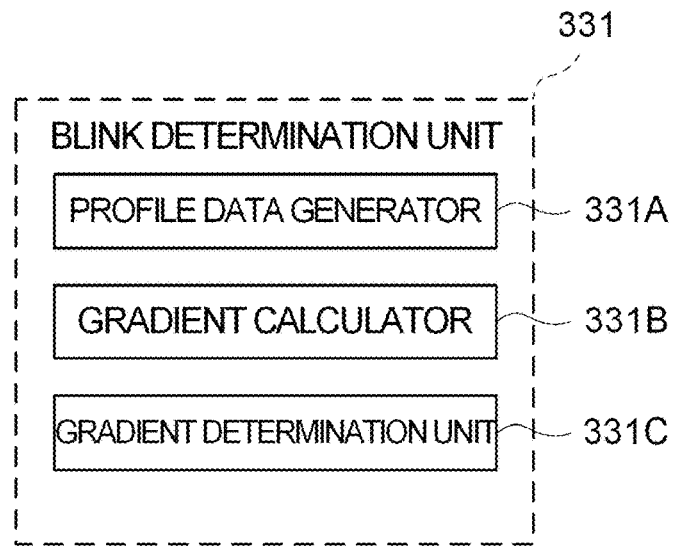
FIG. 5 is a schematic diagram illustrating an example of the configuration of the ophthalmologic imaging apparatus according to the embodiments.
Figure 6:
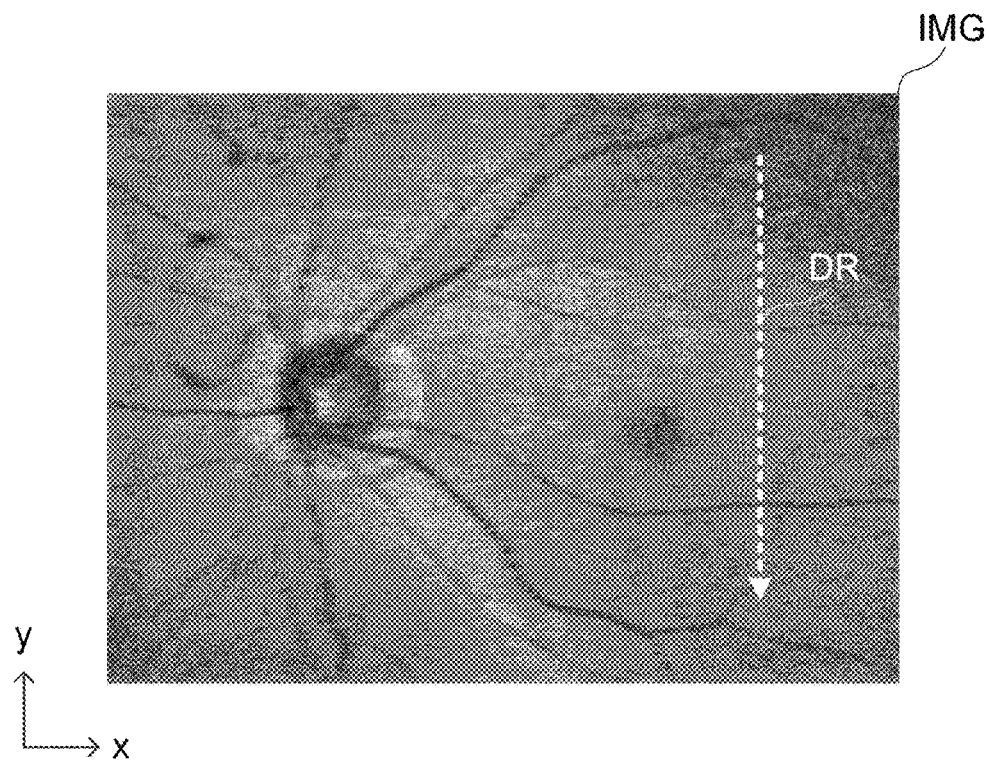
FIG. 6 is a schematic diagram for describing an operation of the ophthalmologic imaging apparatus according to the embodiments.
Figure 7:
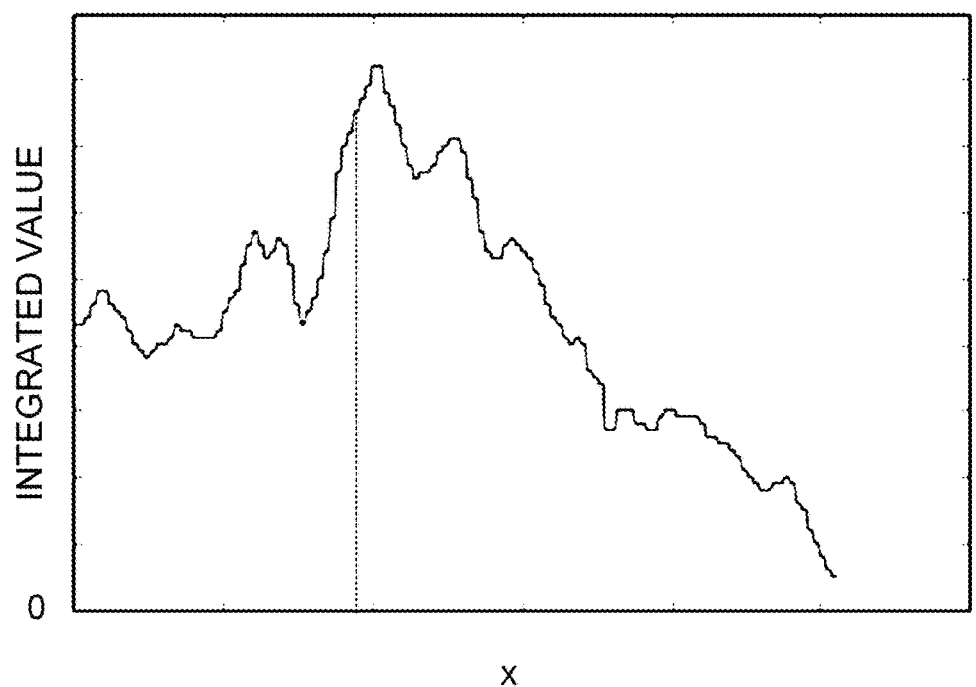
FIG. 7 is a schematic diagram for describing an operation of the ophthalmologic imaging apparatus according to the embodiments.
Figure 8:
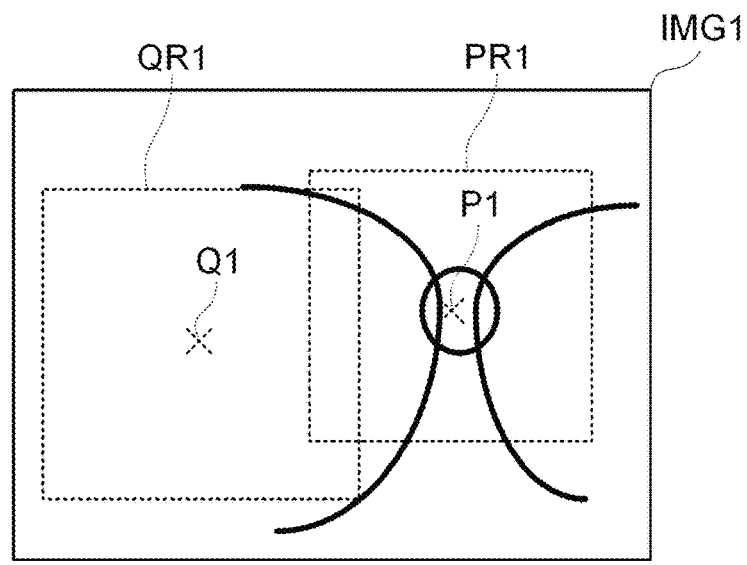
FIG. 8 is a schematic diagram for describing an operation of the ophthalmologic imaging apparatus according to the embodiments.
Figure 9:
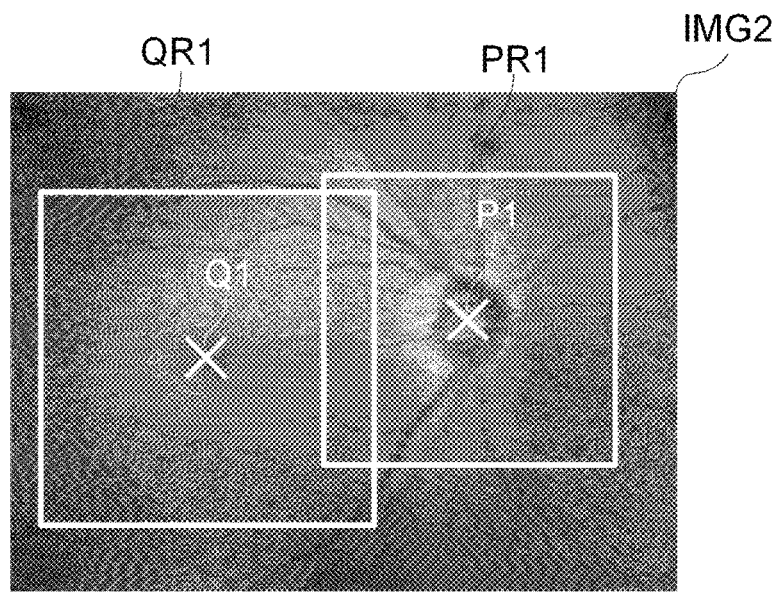
FIG. 9 is a schematic diagram for describing an operation of the ophthalmologic imaging apparatus according to the embodiments.
Figure 10:
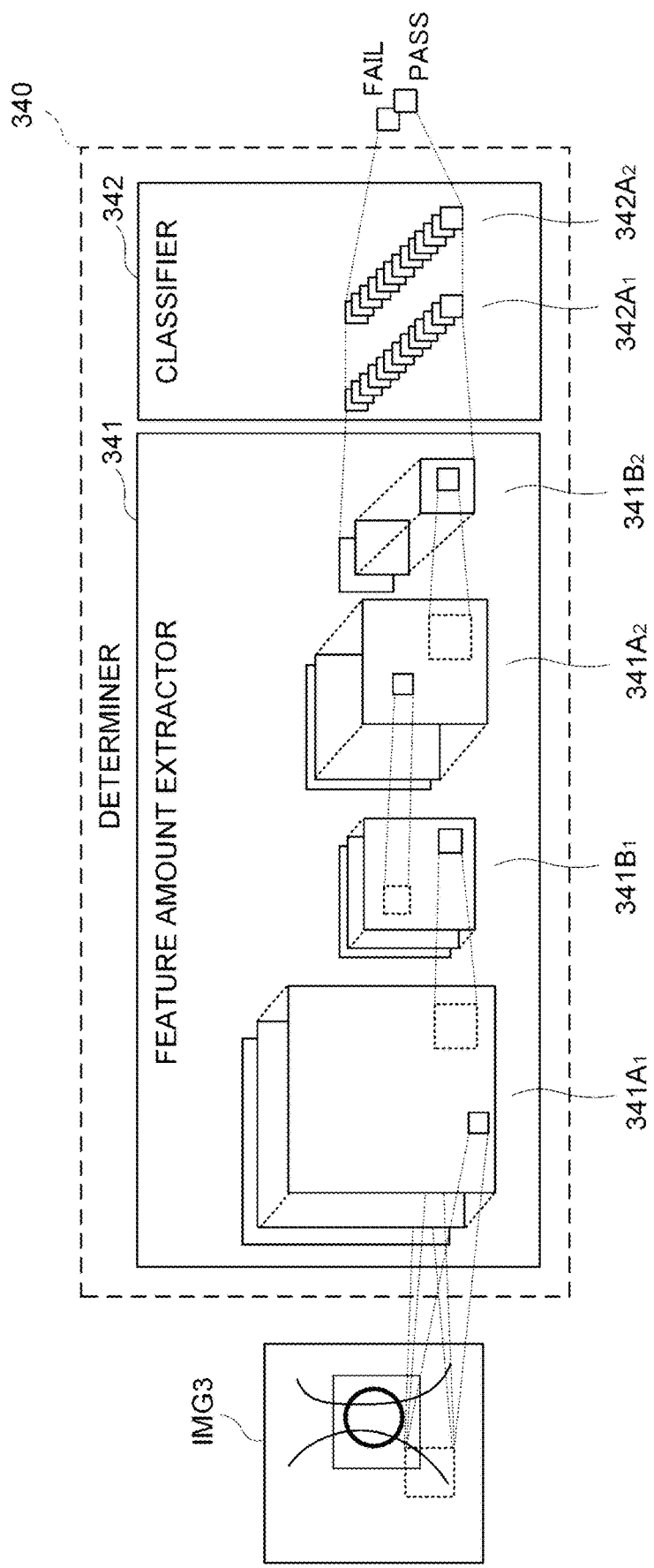
FIG. 10 is a schematic diagram illustrating an example of the configuration of the ophthalmologic imaging apparatus according to the embodiments.
Figure 11:
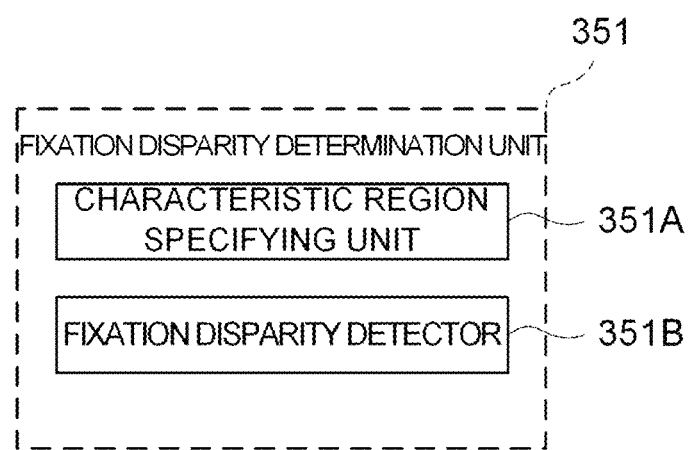
FIG. 11 is a schematic diagram illustrating an example of the configuration of the ophthalmologic imaging apparatus according to the embodiments.

FIGS. 4 to 11 show diagrams describing the of the data processor 300 according to the embodiments. FIG. 4 represents a block diagram of an example of the configuration of the data processor 300 according to the embodiments. FIG. 5 represents a block diagram of an example of the configuration of a blink determination unit 331 in FIG. 4. FIGS. 6 and 7 represent diagrams describing the operation of the blink determination unit 331. FIG. 8 represents a diagram describing the operation of a disc determination unit 332, a fovea determination unit 333, and an analysis region determination unit 334, which are shown in FIG. 4. FIG. 9 represents a diagram describing the operation of a determination image generator 335 in FIG. 4. FIG. 10 represents a block diagram of an example of the configuration of a determiner 340 in FIG. 4. FIG. 11 represents a block diagram of an example of the configuration of a fixation disparity determination unit 351 in FIG. 4.

The data processor 300 determines in a classification unit 320 described later whether or not the acquired image is the analysis error image including the predetermined analysis error factor, before performing the predetermined analysis processing. Here, the predetermined analysis error is an error that may occur in the predetermined analysis processing. Such the data processor 300 includes a projection image forming unit 310, the classification unit (classification processor) 320, and an analyzer 360.

The projection image forming unit 310 forms the projection image described above. The classification unit 320 classifies the projection image formed by the projection image forming unit 310 into either an image suitable for the analysis processing performed by the analyzer 360 on the projection image or an image unsuitable for the analysis processing performed by the analyzer 360 on the projection image. The image suitable for the analysis processing is, for example, an image for which the result of the analysis processing is useful. The classification unit 320 can classify whether or not the result of the analysis processing for the image is useful, by determining whether or not the image to be classified includes an analysis error factor. The analyzer 360 performs the predetermined analysis processing on the projection image which is classified as an image suitable for the predetermined analysis processing by the classification unit 320.

(Projection Image Forming Unit)

The projection image forming unit 310 forms the projection image of the fundus Ef (or the anterior segment Ea) of the subject's eye E using a known method. For example, the projection image forming unit 310 forms the projection image by projecting the volume data of the fundus Ef (or the anterior segment Ea) of the subject's eye E in the z direction.

(Classification Unit)

The classification unit 320 classifies the projection image formed by the projection image forming unit 310 according to the determination criteria (classification criteria) for determining whether or not the image to be classified includes not only the predetermined analysis error factor but also another analysis error factor. Such the classification unit 320 can sequentially perform determination processing on the projection image based on each of the two or more determination criteria.

The classification unit 320 according to the embodiments performs the determination processing on the projection image, according to predetermined determination criteria for determining whether or not the image to be classified includes the predetermined analysis error factor and determination criteria for determining whether or not the image to be classified includes an analysis error factor other than the predetermined analysis error factor. Examples of the predetermined analysis error factor include a blink, failure to specify the characteristic site (failure to detect the characteristic site), a displacement of the analysis range, and a fixation disparity. Examples of the analysis error factor other than the predetermined analysis error factor include a folding back of the imaging site occurred in the captured image when the reference position in the z direction is not appropriate, and an analysis error factor that is statistically or empirically determined to be unsuitable for analysis.

The classification unit 320 includes a preprocessor (pre-processing unit) 330, the determiner 340, and a postprocessor (post-processing unit) 350. The preprocessor 330 and the postprocessor 350 perform the determination processing on the projection image, according to the predetermined determination criteria for determining whether or not the image to be classified includes the predetermined analysis error. The determiner 340 performs the determination processing on the projection image, according to the determination criteria for determining whether or not the image to be classified includes an analysis error factor other than the predetermined analysis error factor. The preprocessor 330 determines whether or not the projection image includes the analysis error factor of any one of the blink, the failure to specify the characteristic site, and the displacement of the analysis range. The characteristic site according to some embodiments includes a disc (optic disc) and a fovea (central fovea). The determiner 340 determines whether or not the projection image includes the folding back of the imaging site occurred in the captured image, or whether or not the projection image includes the analysis error factor that is statistically or empirically determined to be unsuitable for analysis. The postprocessor 350 determines whether or not the projection image includes the fixation disparity as the analysis error factor.

The preprocessor 330 performs the determination processing on the projection image formed by the projection image forming unit 310. The determiner 340 performs the determination processing on the projection image which is determined to be suitable for analysis by the preprocessor 330. The postprocessor 350 performs the determination processing on the projection image which is determined to be suitable for analysis by the determiner 340.

The determination processing performed by the preprocessor 330 allows analysis error images including the analysis error factor that occurs frequently and is clearly depicted in the captured image to be excluded from the target of the analysis processing performed by the analyzer 360 described later. The determination processing performed by the determiner 340 allows analysis error images including various other analysis error factors to be excluded from the target of the analysis processing performed by the analyzer 360 described later. The determination processing performed by the postprocessor 350 allows analysis error images including the predetermined analysis error factor (in particular, local analysis error factor) to be excluded from the target of the analysis processing performed by the analyzer 360 described later, for the projection images that were not determined to be analysis error images by the preprocessor 330 and the determiner 340.

(Preprocessor)

As shown in FIG. 4, the preprocessor 330 includes a blink determination unit 331, a disc determination unit 332, a fovea determination unit 333, an analysis region determination unit 334, and a determination image generator 335.

(Blink Determination Unit)

The blink determination unit 331 determines whether or not the projection image includes the analysis error factor caused by the blink of the subject's eye.

As shown in FIG. 5, the blink determination unit 331 includes a profile data generator 331A, a gradient calculator 331B, and a gradient determination unit 331C.

The profile data generator 331A generates integrated profile data (FIG. 7). The integrated profile data is obtained by integrating luminance profile of the B-scan direction (for example, the x direction of the projection image IMG shown in FIG. 6) in an integrated direction DR (for example, the y direction of the projection image IMG shown in FIG. 6) which intersects (orthogonally) the B-scan direction.

In some embodiments, the profile data generator 331A specifies the luminance profile in the B-scan direction from the image data of the projection image generated by the projection image forming unit 310, and generates the integrated profile data by integrating a plurality of the specified luminance profiles of the B-scan direction in the integrated direction DR.

In some embodiments, the profile data generator 331A generates the luminance profile in the B-scan direction from the reflection intensity profiles for the respective A-lines obtained by performing the Fourier transform etc. on the spectral distribution based on the detection result obtained by the detector 125. For example, the luminance value at the A-scan position is obtained by integrating the reflection intensity values corresponding to a predetermined layer region (or all layer regions in the z direction) in the reflection intensity profile, and the luminance profile in the B-scan direction is generated by forming a data set in the B-scan direction. The profile data generator 331A generates the integrated profile data by integrating a plurality of the generated luminance profile of the B-scan direction in the integrated direction DR.

The gradient calculator 331B calculates a gradient of the integrated profile at one or more positions (pixel position, scan position) in the x direction. As illustrated in FIG. 7, when the horizontal axis represents the position in the x direction and the vertical axis represents the integrated value, the integrated profile represents the integrated value at each position in the x direction.

In some embodiments, the gradient calculator 331B calculates the gradients of the integration profile at all positions in the x direction (B-scan direction). In some embodiments, the gradient calculator 331B calculates the gradients of the integrated profile at two or more positions in the B-scan direction with a predetermined interval.

The gradient determination unit 331C determines the blink or absence thereof from the gradient calculated by the gradient calculator 331B, focusing on the fact that the gradient of the integrated profile becomes steeper at the position where artifacts caused by the blink are depicted. For example, the gradient determination unit 331C specifies representative values of the gradients at two or more positions calculated by the gradient calculator 331B. The gradient determination unit 331C determines that the image is one in which the blink has occurred when the specified representative value is equal to or greater than a predetermined threshold, and determines that the image is one in which the blink has not occurred when the specified representative value is less than the predetermined threshold. Examples of the representative value include the maximum value of the absolute value of the gradient, the average value of the absolute value of the gradient, the median value of the absolute value of the gradient, and the mode value of the absolute value of the gradient.

Further, the gradient determination unit 331C can determine the blink or absence thereof from the gradient calculated by the gradient calculator 331B, focusing on the fact that the steeper the gradient of the integrated profile is, the higher the possibility of the fixation disparity becomes. Also in this case, the gradient determination unit 331C determines that the image is one in which the fixation disparity has occurred when a representative value of the gradient at two or more positions calculated by the gradient calculator 331B is equal to or greater than a predetermined threshold, and determines that the image is one in which the fixation disparity has not occurred when the specified representative value is less than the predetermined threshold.

(Disc Determination Unit)

The disc determination unit 332 performs processing for specifying a region corresponding to the disc (optic disc) in the projection image, and determines whether or not the region corresponding to the disc has been specified.

In some embodiments, the disc determination unit 332 determines whether or not the region corresponding to the disc has been specified in the projection image by analyzing the tomographic image or the three-dimensional image of the fundus Ef to specify the region corresponding to the disc. For example, the disc determination unit 332 analyzes the tomographic image or the three-dimensional image of the fundus Ef to detect a hole (cut, defect site) of the retina, and obtains the shape of the optic disc. The shape of the disc is specified as the image region corresponding to the optic disc and the retinal surface in its vicinity by analyzing the tomographic images, etc., for example. When the shape of the disc is specified, the disc determination unit 332 can specify a position of the projection image IMG1 corresponding to the center position (position of the center of gravity) of the depicted region of the hole in the tomographic image, etc. as the disc position P1, as shown in FIG. 8.

In some embodiments, the disc determination unit 332 analyzes the front image of the fundus Ef such as the projection image and determines whether or not the region corresponding to the disc has been specified. For example, the disc determination unit 332 can specify the contour portion of the optic disc based on the luminance information such as the projection image, and can specify the center position (position of the center of gravity) of the specified contour portion as the position of the disc. In some embodiments, the contour portion is specified using the fact that the shape of the contour region of the disc is circular (oval). In some embodiments, the contour portion is specified by analyzing the shape of the tomographic image of the fundus Ef. In some embodiments, the specifying processing of the contour portion of the optic disc is performed within a search region specified based on the distribution (running state) of blood vessels of a predetermined diameter or larger in the fundus Ef.

In some embodiments, the disc determination unit 332 determines whether or not the region corresponding to the disc has been specified, taking into account whether the subject's eye E is the left eye or the right eye. For example, when the subject's eye is the left eye, the optic disc may be drawn near the left edge of the frame, and when the subject's eye is the right eye, the optic disc may be drawn near the right edge of the frame. Thus, the disc determination unit 332 can perform specifying processing of the region corresponding to the optic disc within the search region specified based on the subject's eye information (information indicating that the subject's eye E is the left eye or the right eye) stored in the storage unit 212, for example.

(Fovea Determination Unit)

The fovea determination unit 333 performs processing for specifying a region corresponding to the fovea in the projection image, and determines whether or not the region corresponding to the fovea has been specified.

In some embodiments, the fovea determination unit 333 determines whether or not the region corresponding to the fovea has been specified in the projection image by analyzing the tomographic image or the three-dimensional image of the fundus Ef to specify the region corresponding to the fovea.

In some embodiments, the fovea determination unit 333 specifies the region corresponding to a macular region of the subject's eye E based on the detection result of the interference light LC obtained by the interference optical system. In some embodiments, the fovea determination unit 333 specifies the region corresponding to the macular region of the subject's eye E by specifying the morphology of the fundus Ef based on the detection result of the interference light LC. For example, the fovea determination unit 333 can specify the region corresponding to the macular region by analyzing the cross-sectional shape of the retina and/or the thickness of the retina from the tomographic image (B-scan image) of the subject's eye E formed by the image forming unit 230. Alternatively, the fovea determination unit 333 can specify the region corresponding to the macular region of the subject's eye E in the three-dimensional image based on the three-dimensional image of the subject's eye E.

In some embodiments, the fovea determination unit 333 analyzes the front image of the fundus Ef such as the projection image and determines whether or not the region corresponding to the fovea has been specified. For examiner, the fovea determination unit 333 performs processing for specifying a region corresponding to the macular region in the projection image, and determines whether or not the region corresponding to the macular region has been specified. When the region corresponding to the macular region is specified, the fovea determination unit 333 can specify a center position (position of the center of gravity) of the specified region in the projection image IMG1 as the fovea position Q1, as shown in FIG. 8.

In some embodiments, the fovea determination unit 333 specifies the region corresponding to the macular region based on the front image of the fundus Ef, and specifies the center of the specified region as the region corresponding to the fovea. The fovea determination unit 333 can specify the region corresponding to the macular region as the group of pixels having a luminance equal to or less than a predetermined threshold in the front image. Alternatively, the fovea determination unit 333 can specify the region corresponding to the macular region with reference to the position of the optic disc specified in the front image by the disc determination unit 332.

(Analysis Region Determination Unit)

The analysis region determination unit 334 determines whether or not the position of the analysis region to be analyzed by the analyzer 360 described later is appropriate. The analysis region can be set with reference to a site of interest automatically or manually. Examples of the site of interest include the position of the disc specified by the disc determination unit 332 and the position of the fovea specified by the fovea determination unit 333. The analysis region is a region, which has a predetermined size, centered on the region of interest. In some embodiments, the shape of the analysis region is a rectangle, a circle, or an arbitrary shape excluding the region designated by the user or the like. In some embodiments, the analysis region is two or more regions that are separated from each other.

In some embodiments, the analysis region determination unit 334 determines whether or not the position of the analysis region is appropriate, by determining whether or not the analysis region is within a predetermined analysis effective range. The predetermined analysis effective range may be a scan range scanned by the measurement light LS deflected by the optical scanner 42. The analysis region determination unit 334 determines that the position of the analysis region is appropriate when the entire analysis region is within the analysis effective range, and determines that the position of the analysis region is not appropriate when at least a part of the analysis region is outside the analysis effective range.

For examples, as shown in FIG. 8, for the analysis region PR1 having a predetermined size centered on the disc position P1 specified by the disc determination unit 332 and the analysis region QR1 having a predetermined size centered on the fovea position Q1 specified by the fovea determination unit 333, the analysis region determination unit 334 determines whether or not the positions of both analysis regions are appropriate. That is, the analysis region determination unit 334 determines that the positions of the analysis regions are appropriate when both of the analysis region PR1 and the analysis region QR1 are within the analysis effective range, and determines that the positions of the analysis regions are not appropriate when at least a part of the analysis region PR1 and the analysis region QR1 is out of the analysis effective.

(Determination Image Generator)

The determination image generator 335 generates the determination image in which analysis information is added to the projection image formed by the projection image forming unit 310. Examples of adding analysis information include attaching analysis information as tags to image data and superimposing analysis information on images. In the present specification, the determination image is a kind of projection image.

Examples of the analysis information include a measurement result of the image of the subject's eye and an analysis result of the image of the subject's eye. The analysis information may include information about the image. Examples of the information about the image include information about the subject, information about the subject's eye, identification information of the apparatus that acquired the image of the subject's eye, information about the acquiring institution (facility) that acquired the image of the subject's eye, and information about the analyzing institution (facility) that analyzes the image of the subject's eye.

In some embodiments, the determination image generator 335 generates the determination image by adding the analysis information to the determination image based on the information stored in storage unit 212. In some embodiments, the determination image generator 335 generates the determination image by adding information corresponding to the analysis result of the projection image obtained by the data processor 300 to the projection image as analysis information. In some embodiments, the determination image generator 335 generates the determination image by adding analysis information generated by an analysis information generator (not shown) to the projection image.

The determination image generator 335 adds the analysis information described above to the projection image determined to be suitable for analysis in all of the blink determination unit 331, the disc determination unit 332, the fovea determination unit 333, and the analysis region determination unit 334.

For example, the determination image generator 335 generates the determination image IMG2 in which the analysis information is added to the projection image IMG1, as shown in FIG. 9. In FIG. 9, the analysis information includes information representing the disc position P1 specified by the disc determination unit 332, information representing the fovea position Q1 specified by the fovea determination unit 333, and information representing the analysis regions PR1, QR1 specified by the analysis region determination unit 334.

(Determiner)

The determiner 340 determines whether or not the determination image (projection image) generated by the determination image generator 335 is the analysis error image.

Here, the analysis error image includes the folding back of the imaging site or the analysis error factor that is statistically or empirically determined to be unsuitable for analysis.

For example, the determiner 340 determines whether or not the determination image is the analysis error image including the folding back of the imaging site as the analysis error factor, by determining whether or not the locus of the position of the folding back the imaging site is drawn so as to intersect any two of the four ends (upper end, lower end, left end, right end) of the frame of the determination image.

For example, the determiner 340 determines whether or not the determination image is the analysis error image including the analysis error factor that is statistically or empirically determined to be unsuitable for analysis, by performing the determination processing on the projection image formed by the projection image forming unit 310 based on the images of eyes of two or more subjects acquired in the past (captured images of the eyes of a plurality of subjects, projection images formed in the past based on the captured images). In this case, the determiner 340 can determine whether or not the determination image is the analysis error image including the folding back of the imaging site as the analysis error factor, without detecting the locus as described above.

In some embodiments, the determiner 340 specifies the determination criteria for determining whether or not the image is the analysis error image by analyzing the images of eyes of two or more subjects acquired in the past. The determiner 340 performs the determination processing on the projection image formed by the projection image forming unit 310, according to the specified determination criteria.

In some embodiments, the determiner 340 performs the determination processing on the projection image formed by the projection image forming unit 310, using a trained model obtained by performing machine learning using the images of eyes of two or more subjects acquired in the past (captured images of the eyes of a plurality of subjects, projection images formed in the past based on the captured images) as training data. The training data may include the determination image (projection image) (FIG. 9) to which the analysis information obtained by analyzing the projection image is added.

Hereinafter, a case where the determiner 340 performs the determination processing on the determination image using the trained model will be described.

The trained model according to the embodiments is used in the computer (processor) including a CPU and a memory. The function of the determiner 340 is realized by a convolutional neural network (CNN), for example. That is, in accordance with the commands from the trained model stored in the memory, the CPU operates so as to perform the calculation based on the learned weighting coefficients and response functions in the convolutional neural network on the pixel values of the determination image input to the convolution layer $341A_1$ of the feature amount extractor 341 described later, which is the input layer, and to output the determination result from the classifier 342 described later, which is the output layer. The determiner 340 having such a configuration can extract a local correlation pattern while gradually reducing the resolution of the determination image, and output the determination result based on the extracted correlation pattern.

FIG. 10 shows a block diagram of an example of the configuration of the determiner 340 according to the embodiments.

The determiner 340 includes the feature amount extractor 341 and the classifier 342. The feature amount extractor 341 repeats the extraction of the feature amount and the downsampling (filtering) for each predetermined image region with respect to the input determination image IMG3 and extracts the feature amount of the determination image. The classifier 342 generates output information indicating whether or not the image is the analysis error image based on the feature amount extracted by the feature amount extractor 341, and outputs information (for example, PASS/FAIL) indication whether or not the determination image is the analysis error image based on the generated output information.

The feature amount extractor 341 includes a plurality of units in which units are connected multiple stages. Each unit includes a convolution layer and a pooling layer. In each unit, the inputs of the pooling layer are connected to the outputs of the convolution layer. The pixel values of the corresponding pixels in the determination image are input to the inputs of the convolution layer in the first stage. The inputs of the convolution layer in the latter stage are connected to the outputs of the pooling layer in the previous stage.

In FIG. 10, the feature amount extractor 341 includes two units connected in two stages. That is, in the feature amount extractor 341, the unit including the convolution layer $341A_2$ and the pooling layer $341B_2$ is connected to the subsequent stage of the unit including the convolution layer $341A_1$ and the pooling layer $341B_1$. The outputs of the pooling layer $341B_1$ are connected to the inputs of the convolution layer $341A_2$.

The classifier 342 includes fully connected layers $342A_1$ and $342A_2$. The outputs of the fully connected layer $342A_1$ is connected to the inputs of the fully connected layer $342A_2$.

In the feature amount extractor 341 and the classifier 342, learned weighting coefficients are assigned between the neurons in the two connected layers. Each neuron performs calculation using a response function on calculation result in which weighting coefficient(s) from one or more input neurons is/are added, and outputs the obtained calculation result to a neuron in the next stage.

The weighting coefficient(s) is/are updated by performing known machine learning using the images of the eyes of the two or more subjects acquired in the past (captured images of the eyes of a plurality of subjects, projection images formed in the past based on the captured images) as training data. The existing weighting coefficient(s) is/are updated by performing machine learning using the images of the eyes of the two or more subjects in the past as training data. That is, in the present embodiment, the analysis information is acquired by analyzing the images of the eyes of the subjects previously acquired. The determination image in which the acquired analysis information is added to the image of the subject's eye is generated. And then, the trained model for determining whether or not the captured image of the subject's eye other than the image of the subject's eye is the analysis error image including the analysis error factor is generated. Examples of the machine learning include supervised learning, unsupervised learning, and reinforcement learning. In some embodiments, the weighting coefficient(s) is/are updated by transfer learning.

The determiner 340 may have a known layered structure such as VGG16, VGG19, InceptionV3, ResNet18, ResNet50. The classifier 342 may have a configuration such as random forest, support vector machine (SVM).

(Postprocessor)

As shown in FIG. 4, the postprocessor 350 includes a fixation disparity determination unit 351.

(Fixation Disparity Determination Unit)

The fixation disparity determination unit 351 determines whether or not the projection image includes the analysis error factor caused by the fixation disparity of the subject's eye.

As shown in FIG. 11, the fixation disparity determination unit 351 includes a characteristic region specifying unit 351A and a fixation disparity detector 351B.

The characteristic region specifying unit 351A specifies a characteristic region in the fundus Ef by analyzing the projection image. Examples of the characteristic region include a region including a characteristic site and a blood vessel. Examples of the characteristic site include a predetermined site such as an optic disc, a fovea, and a diseased site.

The fixation disparity detector 351B detects the fixation disparity or absence thereof based on the characteristic region specified by the characteristic region specifying unit 351A. For example, the fixation disparity detector 351B detects the presence or absence of a region including a positional deviation of a predetermined threshold value or more in a predetermined direction by analyzing the blood vessel region specified by the characteristic region specifying unit 351A. The fixation disparity detector 351B detects that the fixation disparity has occurred when the region is detected, and detects that the fixation disparity has not occurred when the region is not detected.

In some embodiments, the fixation disparity determination unit 351 determines whether or not the projection image is the analysis error image including the analysis error factor caused by the fixation disparity, using a trained model obtained by performing machine learning using the images of the eyes of the two or more subjects acquired in the past as training data, in the same manner as the determiner 340. For example, the function of the fixation disparity determination unit 351 is realized by a convolutional neural network similar to the structure shown in FIG. 10.

As described above, the classification unit 320 classifies the projection image formed by the projection image forming unit 310 into either an image suitable for the analysis processing performed by the analyzer 360 on the projection image or an image not suitable for the analysis processing.

The case where the classification unit 320 performed the determination processing described above on the projection image has been described. However, the configuration according to the embodiments is not limited to this. The classification unit 320 can perform the determination processing described above on the front image of the subject's eye. Examples of the front image include a C-scan image (C-mode image), a shadowgram, a fundus image acquired by the imaging optical system 30, and the like, in addition to the projection image. The C-scan image is acquired by selecting the pixels on the cross section corresponding to the fundus Ef from the three-dimensional data set, in the image forming unit 230 or the data processor 300. The shadowgram is acquire by projecting a part of the three-dimensional data set in a predetermined direction, in the image forming unit 230 or the data processor 300.

(Analyzer)

The analyzer 360 can perform predetermined analysis processing on the projection image determined by the fixation disparity determination unit 351 not to include the analysis error factor caused by the fixation disparity. Examples of the predetermined analysis processing include specifying (identification) of a predetermined site (tissue, lesion) of the subject's eye E; calculation of a distance, area, angle, ratio, or density between designated sites (distance between layers, interlayer distance); calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic disc, a fovea, a macula, and the like. Examples of the predetermined lesion include a leukoma, a hemorrhage, and the like.

The data processor 300 that functions as above includes, for example, a processor described above, a RAM, a ROM, a hard disk drive, a circuit board, and the like. In a storage device such as the hard disk drive, a computer program for causing the processor to execute the functions described above is stored in advance.

(User Interface)

As shown in FIG. 3, the user interface 240 includes the display unit 240A and the operation unit 240B. The display unit 240A includes the aforementioned display device of the arithmetic control unit 200 and/or the display apparatus 3. The operation unit 240B includes the aforementioned operation device of the arithmetic control unit 200. The operation unit 240B may include various kinds of buttons and keys provided on the housing of the ophthalmologic imaging apparatus 1, or provided outside the ophthalmologic imaging apparatus 1. For example, when the fundus camera unit 2 has a case similar to that of the conventional fundus camera, the operation unit 240B may include a joy stick, an operation panel, and the like provided to the case. Further, the display unit 240A may include various kinds of display devices, such as a touch panel placed on the housing of the fundus camera unit 2.

It should be noted that the display unit 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the controller 210 as an electric signal. Moreover, operations and inputs of information may be performed using a graphical user interface (GUI) displayed on the display unit 240A and the operation unit 240B.

The data processor 300 is an example of the "ophthalmologic information processing apparatus" according to the embodiments. The OCT image, the projection image, or the determination image is the "captured image" according to the embodiments. The projection image forming unit 310 is an example of the "acquisition unit" according to the embodiments. The classification unit 320 is an example of the "determination unit" according to the embodiments. The determiner 340 is an example of the "first determination unit" according to the embodiments. The preprocessor 330 is an example of the "second determination unit" according to the embodiments. At least one of the disc determination unit 332 and the fovea determination unit 333 is an example of the "characteristic site determine unit" according to the embodiments. The analysis region determination unit 334 is an example of the "region determination unit" according to the embodiments. The postprocessor 350 is an example of the "third determination unit" according to the embodiments. The OCT unit 100 and the image forming unit 230 (and/or the data processor 300) are examples of the "imaging unit" according to the embodiments.

[Operation]

The operation of the ophthalmologic imaging apparatus 1 according to the first embodiment will be described.

Figure 12:
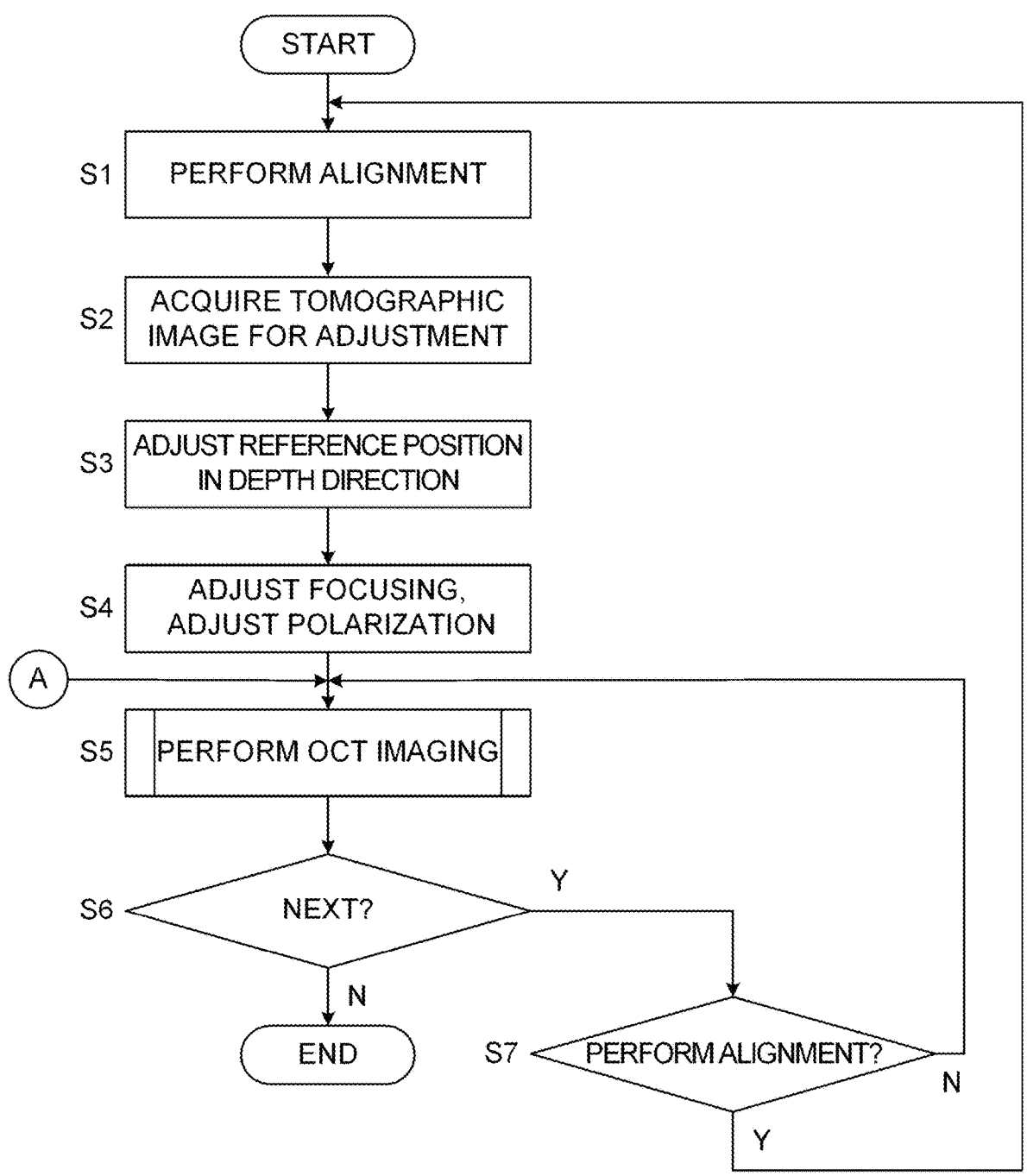
FIG. 12 is a flowchart illustrating an example of the operation of the ophthalmologic imaging apparatus according to the embodiments.
Figure 13:
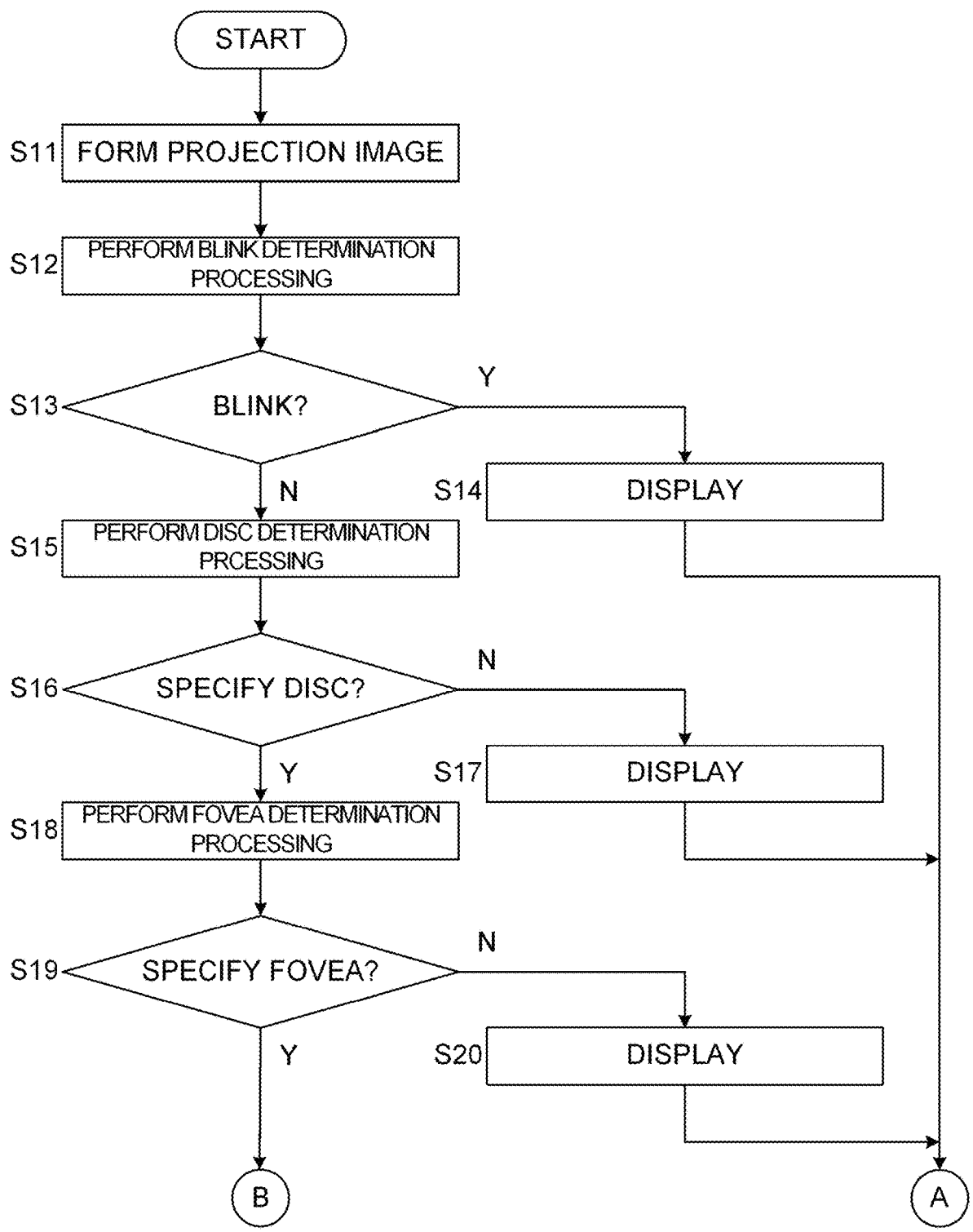
FIG. 13 is a flowchart illustrating an example of the operation of the ophthalmologic imaging apparatus according to the embodiments.
Figure 14:
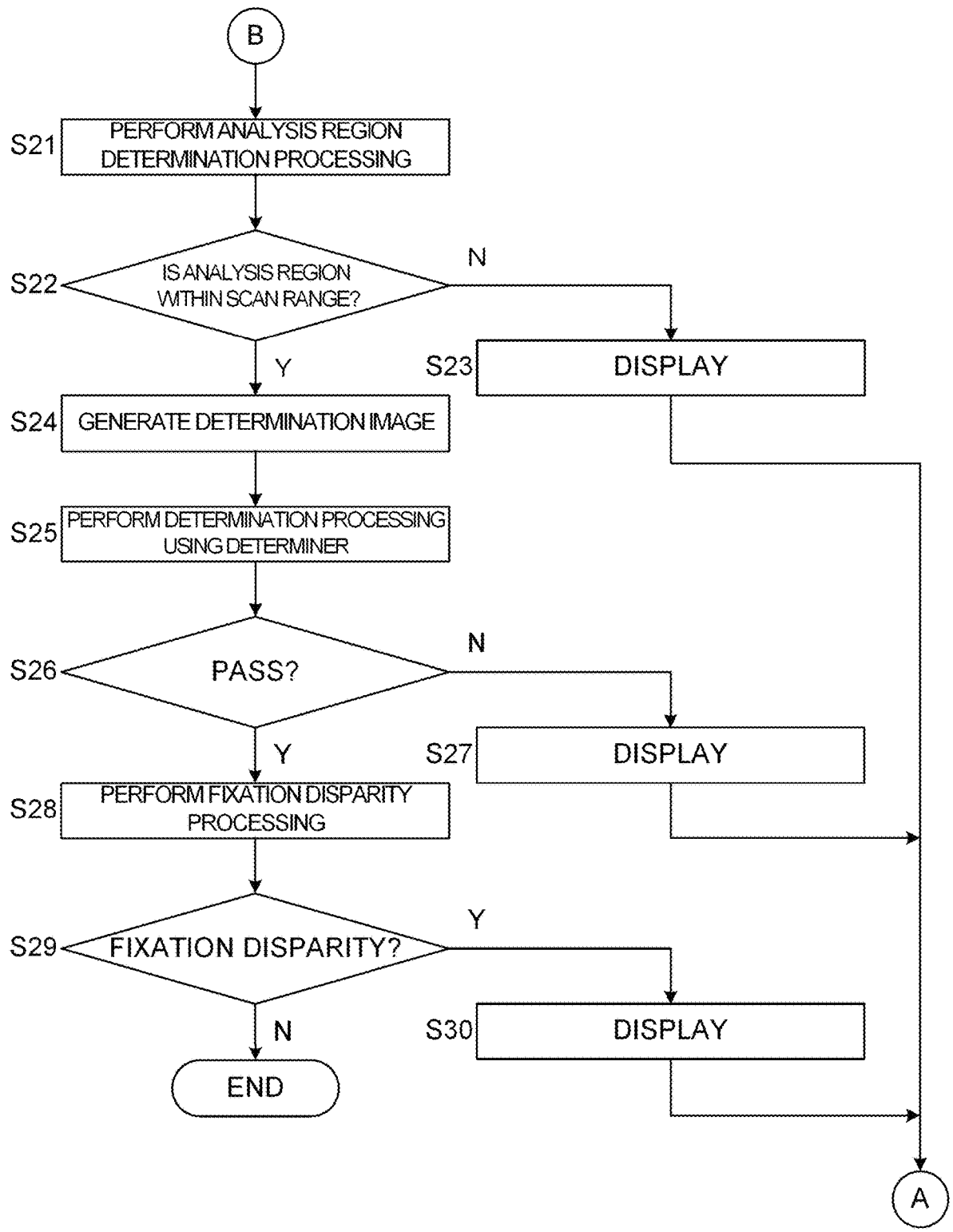
FIG. 14 is a flowchart illustrating an example of the operation of the ophthalmologic imaging apparatus according to the embodiments.

FIGS. 12 to 14 show examples of the operation of the ophthalmologic imaging apparatus 1 according to the first embodiment. FIGS. 12 to 14 show flowcharts of the examples of the operation of the ophthalmologic imaging apparatus 1 according to the first embodiment. The storage unit 212 stores computer programs for realizing the processing shown in FIGS. 12 to 14. The main controller 211 operates according to the computer programs, and thereby the main controller 211 performs the processing shown in FIGS. 12 to 14.

(S1: Perform Alignment)

The main controller 211 performs alignment.

That is, the main controller 211 controls the alignment optical system 50 to project the alignment indicator onto the subject's eye E. At this time, a fixation target generated by the LCD 39 is also projected onto the subject's eye E. The main controller 211 controls the movement mechanism 150 based on the movement amount of the optical system to relatively to move the optical system with respect to the subject's eye E by the movement amount. The movement amount is specified based on the receiving light image obtained using the image sensor 35, for example. The main controller 211 repeatedly performs this processing.

(S2: Acquire Tomographic Image for Adjustment)

The main controller 211 controls the LCD 39 to display the fixation target for OCT measurement at a predetermined position on the LCD 39. The main controller 211 can display the fixation target at a display position on the LCD 39 corresponding to a position of an optical axis of the optical axis on the fundus Ef.

Subsequently, the main controller 211 controls the OCT unit 100 to perform OCT provisional measurement, and to acquire a tomographic image for adjustment for adjusting the reference position of the measurement range in the depth direction. Specifically, the main controller 211 controls the optical scanner 42 to deflect the measurement light LS generated based on the light L0 emitted from the light source unit 101 and to scan a predetermined site (for example, fundus) of the subject's eye E with the deflected measurement light LS. The detection result of the interference light obtained by scanning with the measurement light LS is sent to the image forming unit 230 after being sampled in synchronization with the clock KC. The image forming unit 230 forms the tomographic image (OCT image) of the subject's eye E from the obtained interference signal.

(S3: Adjust Reference Position in Depth Direction)

Subsequently, the main controller 211 adjusts the reference position of the measurement range in the depth direction (z direction).

For example, the main controller 211 controls the data processor 300 to specify a predetermined site (for example, sclera) in the tomographic image obtained in step S2, and sets a position separated by a predetermined distance in the depth direction from the specified position of the predetermined site as the reference position of the measurement range. Alternatively, a predetermined position determined in advance so that the optical path lengths of the measurement light LS and the reference light LR substantially coincide may be set as the reference position of the measurement range.

(S4: Adjust Focusing, Adjust Polarization)

Next, the main controller 211 performs control of adjusting focusing and of adjusting polarization.

For example, the main controller 211 controls the OCT unit 100 to perform OCT measurement, after controlling the focusing driver 43A to move the OCT focusing lens 43 by a predetermined distance. The main controller 211 controls the data processor 300 to determine the focus state of the measurement light LS based on the detection result of the interference light acquired by the OCT measurement, as described above. When it is determined that the focus state is not appropriate based on the determination result of the data processor 300, the main controller 211 controls the focusing driver 43A again and repeats this until it is determined that the focus state of the measurement light LS is appropriate.

Further, for example, the main controller 211 controls the OCT unit 100 to perform OCT measurement after controlling at least one of the polarization controllers 103 and 118 to change the polarization state of at least one of the light L0 and the measurement light LS by a predetermined amount. And then, the main controller 211 controls the image forming unit 230 to form the OCT image on the basis of the acquired detection result of the interference light. The main controller 211 controls the data processor 300 to determine the image quality of the OCT image acquired by the OCT measurement. When it is determined that the polarization state is not appropriate based on the determination result of the data processor 300, the main controller 211 controls the polarization controllers 103 and 118 again and repeats this until it is determined that the polarization state of the measurement light LS is appropriate.

(S5: Perform OCT Imaging)

Subsequently, the main controller 211 controls the OCT unit 100 to perform OCT imaging. Details of step S5 will be described later.

(S6: Next?)

Following step S5, the main controller 211 determines whether or not to continue the OCT imaging. The main controller 211 determines whether or not to continue the OCT imaging according to the operation content of the user with respect to the operation unit 240B or the content of the operation mode set in advance.

When it is determined that the OCT image is to be continued (S6: Y), the operation of the ophthalmologic imaging apparatus 1 proceeds to step S7. When it is determined that the OCT imaging is not to be continued (S6: N), the ophthalmologic imaging apparatus 1 terminates the operation (END).

(S7: Perform Alignment?)

When it is determined in step S6 that the OCT imaging is to be continued (S6: Y), the main controller 211 determines whether or not to re-perform the alignment before the OCT imaging. The main controller 211 determines whether or not to re-perform the alignment according to the operation content of the user with respect to the operation unit 240B, the content of the operation mode set in advance, or the positional relationship between the subject's eye E and the optical system detected by a detection means (not shown).

When it is determined that the alignment is to be re-performed (S7: Y), the operation of the ophthalmologic imaging apparatus 1 proceeds to step S1. When it is determined that the alignment is not to be re-perform (S7: N), the operation of the ophthalmologic imaging apparatus 1 proceeds to step S5.

In step S5 in FIG. 12, the following processing is performed.

(S11: Form Projection Image)

In step S5, first, the main controller 211 controls the OCT unit 100 to perform OCT measurement. The detection result of the interference light acquired by the OCT measurement is sampled by the DAQ 130 and is stored as the interference signal in the storage unit 212 or the like.

Subsequently, the main controller 211 controls the projection image forming unit 310 to form the projection image of the subject's eye E.

(S12: Perform Blink Determination Processing)

Subsequently, the main controller 211 controls the blink determination unit 331 to perform the blink determination processing on the projection image formed in step S11.

(S13: Blink?)

When it is determined that the projection image formed in step S11 is the analysis error image including the analysis error factor caused by the blink by performing the blink determination processing in step S12 (S13: Y), the operation of the ophthalmologic imaging apparatus 1 proceeds to step S14.

When it is determined that the projection image is not the analysis error image (S13: N), the operation of the ophthalmologic imaging apparatus 1 proceeds to step S15.

(S14: Display)

When it is determined in step S13 that the projection image is the analysis error image (S13: Y), the main controller 211 controls the display unit 240A to display controller configured to display information indicating unsuitability for analysis and information indicating that re-imaging will be performed. After that, the operation of the ophthalmologic imaging apparatus 1 proceeds to step S5.

In some embodiments, in the OCT re-imaging when proceeding from step S14 to step S5, the imaging conditions are changed to suppress the occurrence of the analysis error factor caused by blink (e.g., changing the imaging rate and/or the imaging timing).

(S15: Perform Disc Determination Processing)

When it is determined in step S13 that the projection image is not the analysis error image (S13: N), the main controller 211 controls the disc determination unit 332 to perform the disc determination processing on the projection image determined not to be the analysis error image in step S13.

(S16: Specify Disc?)

When it is determined that the projection image is the analysis error image including the analysis error factor caused by the fact that the disc is not detected in the disc determination processing in step S15 (S16: N), the operation of the ophthalmologic imaging apparatus 1 proceeds to step S17.

When it is determined that the projection image is not the analysis error image (S16: Y), the operation of the ophthalmologic imaging apparatus 1 proceeds to step S18.

(S17: Display)

When it is determined in step S16 that the projection image is the analysis error image (S16: N), the main controller 211 controls the display unit 240A to display information indicating unsuitability for analysis and information indicating that re-imaging will be performed. After that, the operation of the ophthalmologic imaging apparatus 1 proceeds to step S5.

In some embodiments, in the OCT re-imaging when proceeding from step S17 to step S5, the imaging conditions are changed to suppress the occurrence of the analysis error factor caused by the fact that the disc is not detected (e.g., changing the imaging site, light amount, and/or light reception sensitivity).

(S18: Perform Fovea Determination Processing)

When it is determined in step S16 that the projection image is not the analysis error image (S16: Y), the main controller 211 controls the fovea determination unit 333 to perform the fovea determination processing on the projection image determined not to be the analysis error image in step S16.

(S19: Specify Fovea?)

When it is determined that the projection image is the analysis error image including the analysis error factor caused by the fact that the fovea is not detected in the fovea determination processing in step S18 (S19: N), the operation of the ophthalmologic imaging apparatus 1 proceeds to step S20.

When it is determined that the projection image is not the analysis error image (S19: Y), the operation of the ophthalmologic imaging apparatus 1 proceeds to step S21.

(S20: Display)

When it is determined in step S19 that the projection image is the analysis error image (S19: N), the main controller 211 controls the display unit 240A to display information indicating unsuitability for analysis and information indicating that re-imaging will be performed. After that, the operation of the ophthalmologic imaging apparatus 1 proceeds to step S5.

In some embodiments, in the OCT re-imaging when proceeding from step S19 to step S5, the imaging conditions are changed to suppress the occurrence of the analysis error factor caused by the fact that the fovea is not detected (e.g., changing the imaging site, light amount, and/or light reception sensitivity).

(S21: Perform Analysis Region Determination Processing)

When it is determined in step S19 that the projection image is not the analysis error image (S19: Y), the main controller 211 controls the analysis region determination unit 334 to perform the analysis region determination processing on the projection image determined not to be the analysis error image in step S19.

(S22: Is Analysis Region within Scan Range?)

When it is determined that the projection image is the analysis error image including the analysis error factor caused by the position of the analysis region in the analysis region determination processing in step S21 (S22: N), the operation of the ophthalmologic imaging apparatus 1 proceeds to step S23.

When it is determined that the projection image is not the analysis error image (S22: Y), the operation of the ophthalmologic imaging apparatus 1 proceeds to step S24.

(S23: Display)

When it is determined in step S22 that the projection image is the analysis error image (S22: N), the main controller 211 controls the display unit 240A to display information indicating unsuitability for analysis and information indicating that re-imaging will be performed. After that, the operation of the ophthalmologic imaging apparatus 1 proceeds to step S5.

In some embodiments, in the OCT re-imaging when proceeding from step S23 to step S5, the imaging conditions are changed to suppress the occurrence of the analysis error factor caused by the position of the analysis region (e.g. changing the fixation position, the scan range, and/or the scan position).

(S24: Generate Determination Image)

When it is determined in step S22 that the projection image is not the analysis error image (S22: Y), the main controller 211 controls the determination image generator 335 to generate the determination image based on the projection image determined not to be the analysis error image in step S22. For example, the determination image generator 335 generates the determination image in which the analysis information obtained by analyzing the projection image is superimposed on the projection image, as shown in FIG. 9.

(S25: Perform Determination Processing Using Determiner)

Subsequently, the main controller 211 controls the determiner 340 to perform the determination processing for determining whether or not the determination image generated in step S24 is the analysis error image.

The determiner 340 can output information corresponding to the determination result of whether or not the input determination image is the analysis error image, with the above configuration. The output information includes pass information indicating that the determination image is determined not to be the analysis error image and fail information indicating that the input determination image is determined to be the analysis error image.

(S26: Pass?)

When it is determined that the projection image is the analysis error image based on the output information from the determiner 340 (S26: N), the operation of the ophthalmologic imaging apparatus 1 proceeds to step S27.

When it is determined that the determination image is not the analysis error image (S26: Y), the operation of the ophthalmologic imaging apparatus 1 proceeds to step S28.

(S27: Display)

When it is determined in step S26 that the determination image is the analysis error image (S26: N), the main controller 211 controls the display unit 240A to display information indicating unsuitability for analysis and information indicating that re-imaging will be performed. After that, the operation of the ophthalmologic imaging apparatus 1 proceeds to step S5.

In some embodiments, in the OCT re-imaging when proceeding from step S27 to step S5, the imaging conditions are changed.

(S28: Perform Fixation Disparity Determination Processing)

When it is determined in step S26 that the projection image is not the analysis error image (S26: Y), the main controller 211 controls the fixation disparity determination unit 351 to perform the fixation disparity determination processing on the determination image determined not to be the analysis error image in step S26.

(S29: Fixation Disparity?)

When it is determined that the determination image is the analysis error image including the analysis error factor caused by the fixation disparity in the fixation disparity determination processing in step S28 (S29: Y), the operation of the ophthalmologic imaging apparatus 1 proceeds to step S30.

When it is determined that the determination image is not the analysis error image (S29: N), the operation of the ophthalmologic imaging apparatus 1 proceeds to step S5.

(S30: Display)

When it is determined in step S29 that the determination image is the analysis error image (S29: Y), the main controller 211 controls the display unit 240A to display information indicating unsuitability for analysis and information indicating that re-imaging will be performed. After that, the operation of the ophthalmologic imaging apparatus 1 proceeds to step S5.

In some embodiments, in the OCT re-imaging when proceeding from step S30 to step S5, the imaging conditions are changed to suppress the occurrence of the analysis error factor caused by the fixation disparity (e.g., changing the fixation position, the imaging rate and/or imaging timing).

Figure 15:
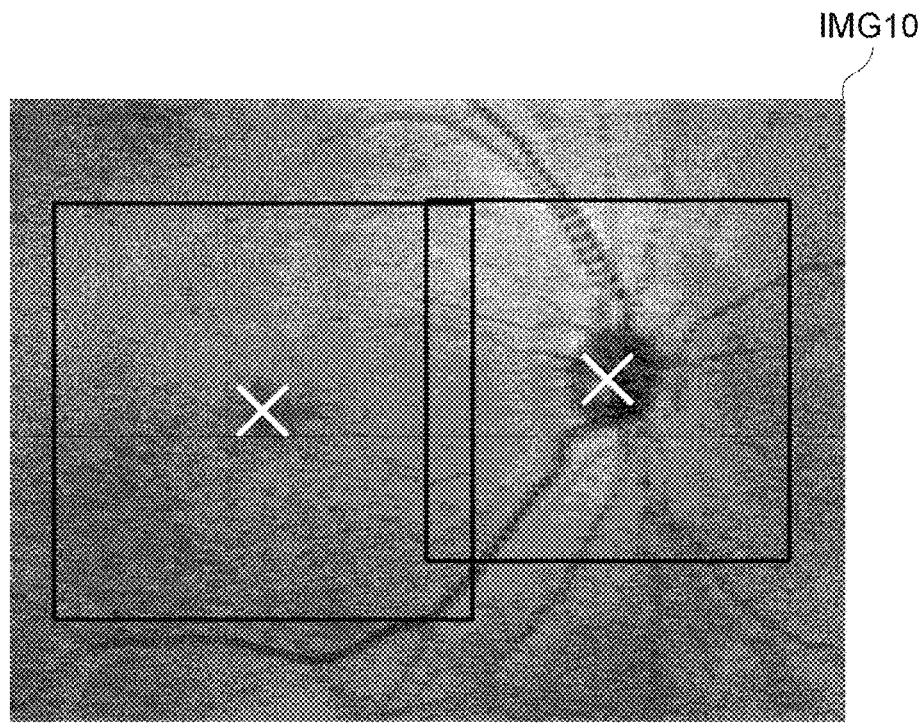
FIG. 15 is a schematic diagram for describing an operation of the ophthalmologic imaging apparatus according to the embodiments.
Figure 16:
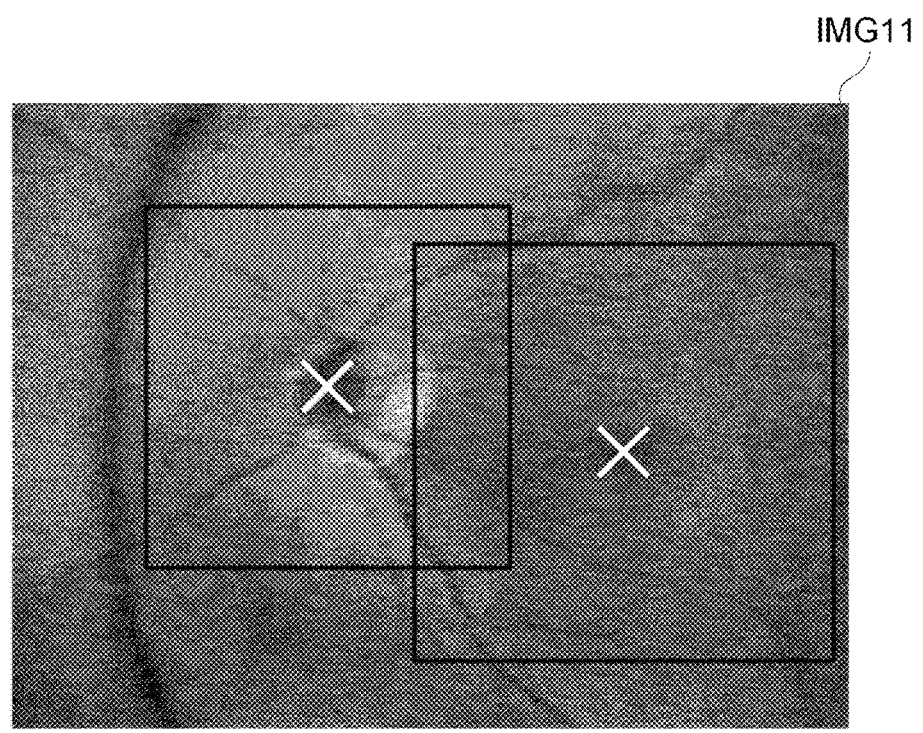
FIG. 16 is a schematic diagram for describing an operation of the ophthalmologic imaging apparatus according to the embodiments.

By performing the above processing, it is possible to classify the determination image IMG10, which is determined not to include the analysis error factor as shown in FIG. 15, and the determination image IMG11, which is determined to include the analysis error factor (folding back of the imaging site) as shown in FIG. 16, before the analysis process.

The main controller 211 controls the analyzer 360 to perform a predetermined analysis processing on the determination image determined not to be the analysis error image in step S29. This allows to prevent the analysis error of the captured image of the subject's eye, on which the analysis processing is performed, and to efficiently acquire the image of the subject's eye suitable for analysis.

Second Embodiment

In the first embodiment, the case where immediately after the acquisition of the captured image by the ophthalmologic imaging apparatus to which the ophthalmologic information processing apparatus according to the embodiments is applied, the image is determined (presumed, predicted) whether or not to be suitable for analysis (usefulness of the analysis result). However, the configuration according to the embodiments is not limited thereto.

In the second embodiment, the ophthalmologic information processing apparatus according to the embodiments can be provided separately from the ophthalmologic imaging apparatus, and can perform the determination processing of the analysis error described above on the captured images acquired by one or more ophthalmologic imaging apparatuses. In the following, the second embodiment is described with a focus on differences from the first embodiment.

Figure 17:
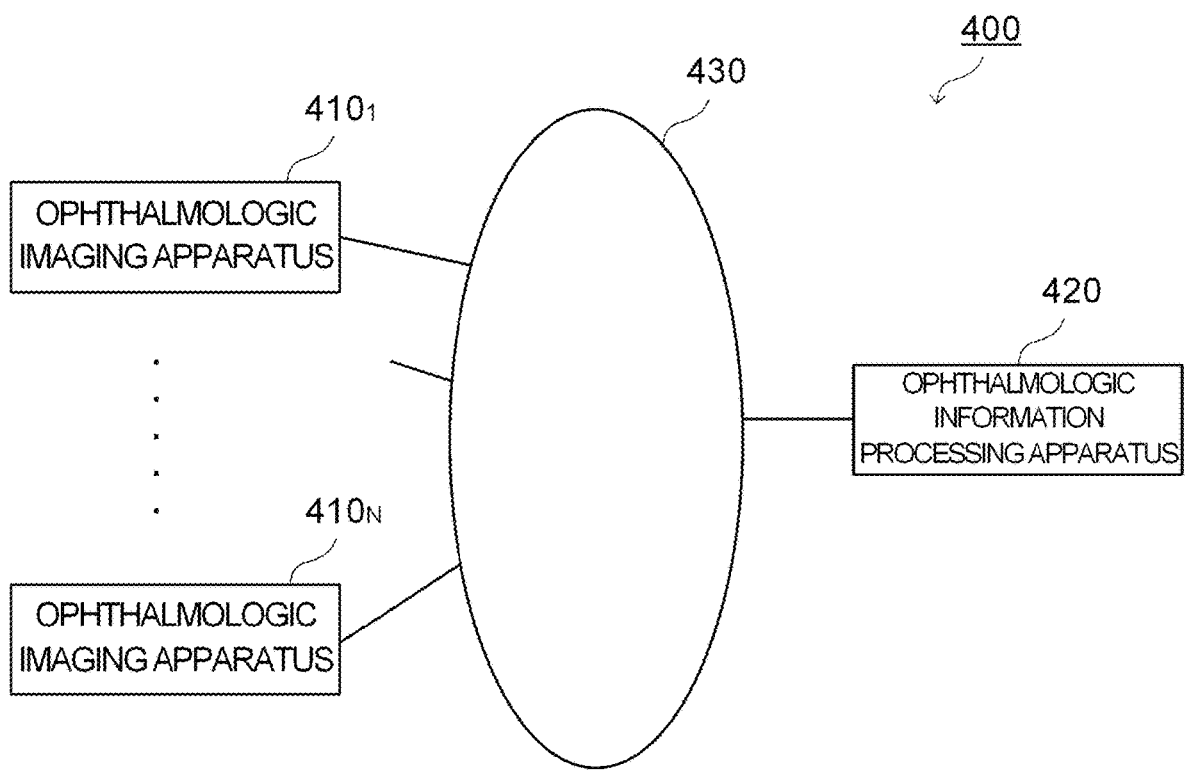
FIG. 17 is a schematic diagram illustrating an example of the configuration of an ophthalmologic system according to the embodiments.

FIG. 17 shows a block diagram of a first configuration example of the ophthalmologic system according to the second embodiment.

The ophthalmologic system 400 according to the first configuration example includes ophthalmologic imaging apparatuses $410_1$ to $410_N$ (N is an integer of 2 or more) and an ophthalmologic information processing apparatus 420. The ophthalmologic information processing apparatus 420 is connected to the ophthalmologic imaging apparatuses $410_1$ to $410_N$ via the network 430. The network 430 may be a wired or wireless network (LAN, WAN).

The ophthalmologic information processing apparatus 420 can communicate with any of the ophthalmologic imaging apparatus $410_1$ to $410_N$.

In some embodiments, any of the ophthalmologic imaging apparatus $410_1$ to $410_N$ transmits a request to the ophthalmologic information processing apparatus 420, and the ophthalmologic imaging apparatus to which the request is approved transmits data to the ophthalmologic information processing apparatus 420. The transmitted data includes image data of the OCT image as the captured image of the fundus Ef or the anterior segment Ea.

In some embodiments, the ophthalmologic information processing apparatus 420 transmits a request to any of the ophthalmologic imaging apparatuses $410_1$ to $410_N$, and receives data from the ophthalmologic imaging apparatus that approves the request. The received data includes image data of the OCT image as the captured image of the fundus Ef or the anterior segment Ea.

Figure 18:
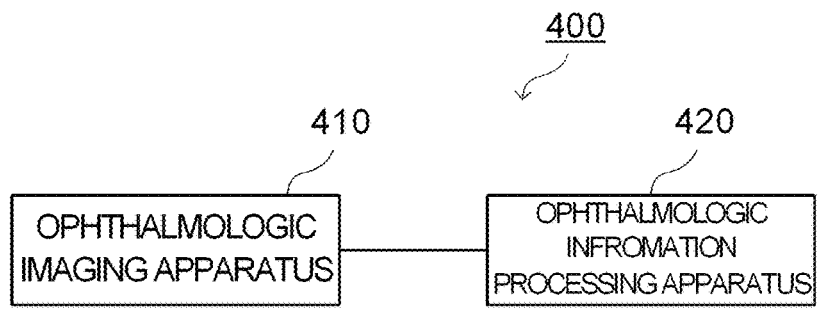
FIG. 18 is a schematic diagram illustrating an example of the configuration of an ophthalmologic system according to embodiments.

FIG. 18 shows a block diagram of a second configuration example of the ophthalmologic system according to the second embodiment.

The ophthalmologic system 400 according to the second configuration example includes the ophthalmologic imaging apparatus 410 and the ophthalmologic information processing apparatus 420. The ophthalmologic information processing apparatus 420 is connected to the ophthalmologic imaging apparatus 410 via a predetermined communication path. In some embodiments, the ophthalmologic information processing apparatus 420 is peer-to-peer connected to the ophthalmologic imaging apparatus 410 via a network.

The ophthalmologic information processing apparatus 420 can communicate with the ophthalmologic imaging apparatus 410.

In some embodiments, the ophthalmologic imaging apparatus 410 transmits a request to the ophthalmologic information processing apparatus 420, and the ophthalmologic imaging apparatus 410 to which the request is approved transmits data to the ophthalmologic information processing apparatus 420. The transmitted data includes image data of the captured image.

In some embodiments, the ophthalmologic information processing apparatus 420 transmits a request to the ophthalmologic imaging apparatus 410, and receives data from the ophthalmologic imaging apparatus 410 that approves the request. The received data includes image data of the captured image.

The ophthalmologic imaging apparatuses $410_1$ to $410_N$ and the ophthalmologic imaging apparatus 410 have substantially the same configurations as the ophthalmologic imaging apparatus 1 shown in FIGS. 1 to 3. In the second embodiment, a part of the functions of the data processor 300 among the functions of the ophthalmologic imaging apparatus 1 shown in FIGS. 1 to 3 is realized by the ophthalmologic information processing apparatus 420.

Figure 19:
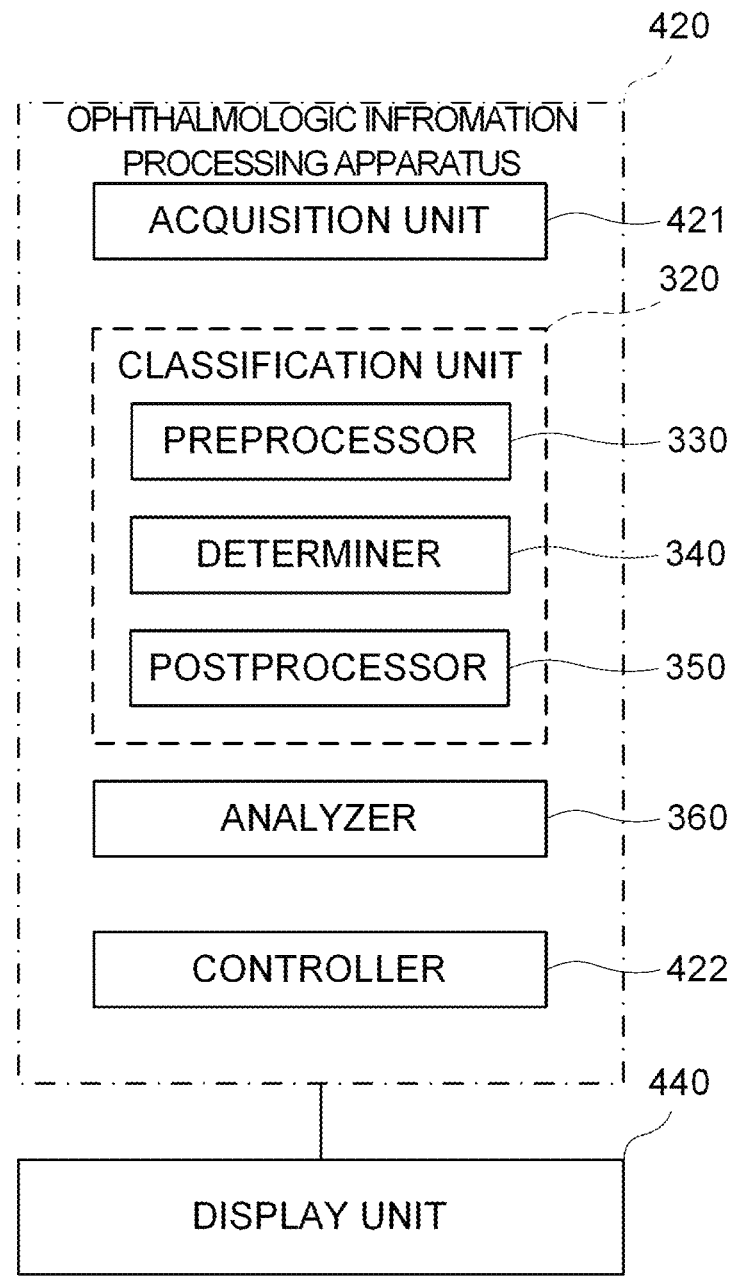
FIG. 19 is a schematic diagram illustrating an example of the configuration of the ophthalmologic information processing apparatus according to the embodiments.

FIG. 19 shows a block diagram of an example of the configuration of the ophthalmologic information processing apparatus 420 according to the second embodiment. In FIG. 19, parts similar to those in FIG. 4 are denoted by the same reference symbols, and description thereof is omitted as appropriate.

The ophthalmologic information processing apparatus 420 includes an acquisition unit 421, the classification unit 320, the analyzer 360 and a controller 422. The classification unit 320 includes the preprocessor 330, the determiner 340, and the postprocessor 350, similar to FIG. 4.

The acquisition unit 421 perform interface processing with the ophthalmologic imaging apparatus $410_1$ to $410_N$ or the ophthalmologic imaging apparatus 410. That is, the acquisition unit 421 communicates with the ophthalmologic imaging apparatuses $410_1$ to $410_N$ or the ophthalmologic imaging apparatus 410 according to a predetermined communication protocol, and receives the communication data including the image data of the captured image from the ophthalmologic imaging apparatuses $410_1$ to $410_N$ or the ophthalmologic imaging apparatus 410. The acquisition unit 421 acquires the captured image (OCT image) of the subject's eye photographed by the ophthalmologic imaging apparatus, by receiving the image data included in the received communication data.

The controller 422 includes a processor and controls each part of the ophthalmologic information processing apparatus 420, in the same manner as the controller 210. The controller 422 includes a main controller and a storage unit, in the same manner as the controller 210.

Further, the controller 422 can perform display control on a display unit 440 connected to the outside of the ophthalmologic information processing apparatus 420, as a display controller. The display unit 440 has the same function as the display unit 240A.

[Operation]

The operation of the ophthalmologic information processing apparatus 420 according to the second embodiment will be described.

Figure 20:
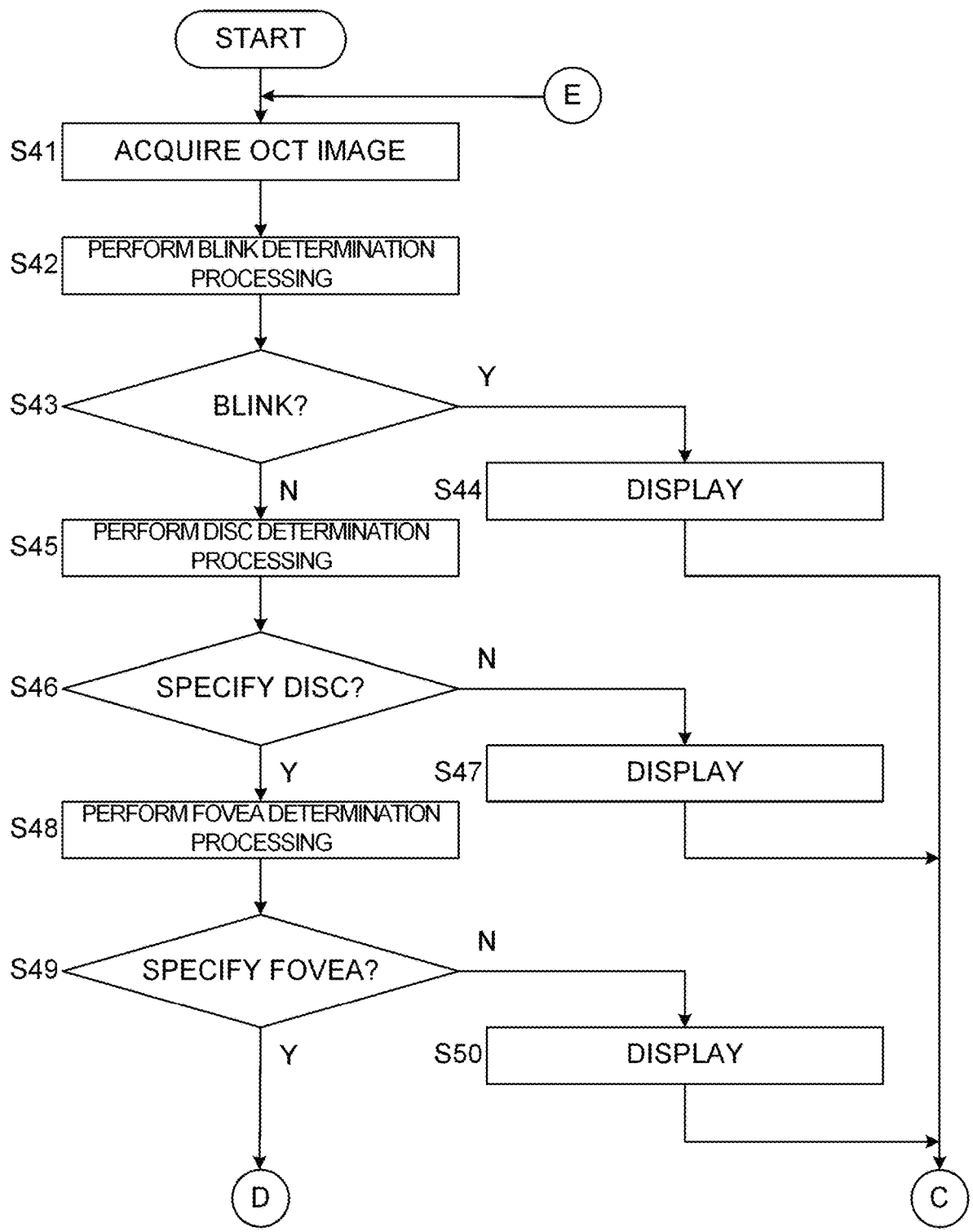
FIG. 20 is a flowchart illustrating an example of an operation of the ophthalmologic information processing apparatus according to the embodiments.
Figure 21:
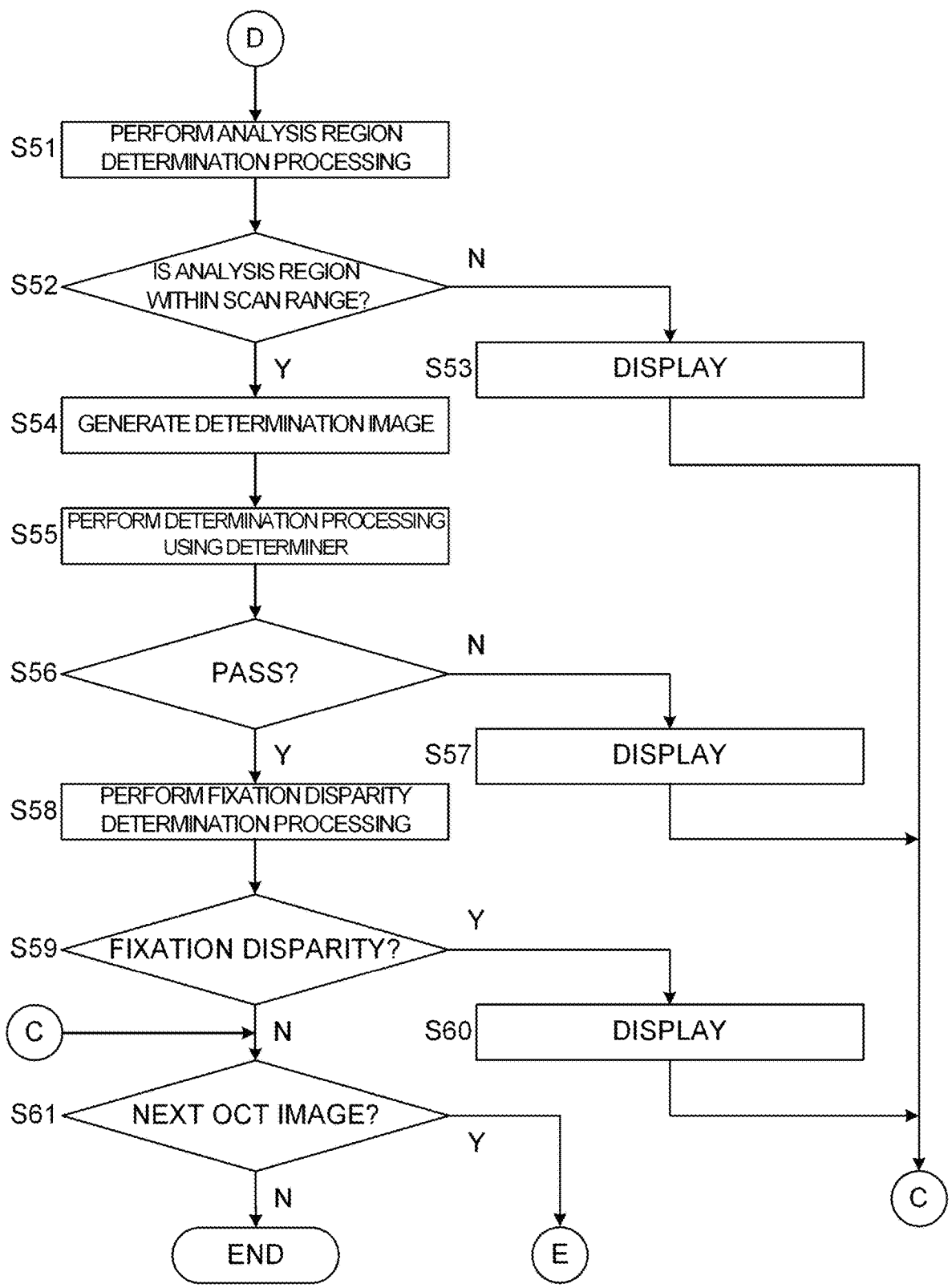
FIG. 21 is a flowchart illustrating an example of an operation of the ophthalmologic information processing apparatus according to the embodiments.

FIGS. 20 and 21 show examples of the operation of the ophthalmologic information processing apparatus 420 according to the second embodiment. FIGS. 20 and 21 show flowcharts of the example of the operation of the ophthalmologic information processing apparatus 420 according to the second embodiment. The storage unit in the controller 422 stores computer program(s) for realizing the processing shown in FIGS. 20 and 21. The main controller in the controller 422 performs the processing shown in FIGS. 20 and 21 by operating according to the computer programs.

(S41: Acquire OCT Image)

The controller 422 controls the acquisition unit 421 to receive the communication data including the image data of the OCT image from any of the ophthalmologic imaging apparatuses $410_1$ to $410_N$ or the ophthalmologic imaging apparatus 410. For example, the controller 422 receives the communication data transmitted from any of the ophthalmologic imaging apparatuses $410_1$ to $410_N$ or the ophthalmologic imaging apparatus 410 by communication interface processing by performed by the acquisition unit 421, and extracts the image data of the OCT image (projection image) from the received communication data.

In some embodiments, the acquisition unit 421 forms the OCT image from the received communication data. For example, the acquisition unit 421 extracts the detection data of the interference light LC from the communication data, and forms the OCT image from the extracted detection data, just like the image forming unit 230 and the data processor 300 shown in FIG. 4.

(S42: Perform Blink Determination Processing)

Subsequently, the controller 422 controls the blink determination unit 331 to perform the blink determination processing on the projection image formed in step S41, in the same manner as in step S12.

(S43: Blink?)

When it is determined that the projection image acquire in step S41 is the analysis error image including the analysis error factor caused by the blink by performing the blink determination processing in step S42 (S43: Y), the operation of the ophthalmologic information processing apparatus 420 proceeds to step S44.

When it is determined that the projection image is not the analysis error image (S43: N), the operation of the ophthalmologic information processing apparatus 420 proceeds to step S45.

(S44: Display)

When it is determined in step S43 that the projection image is the analysis error (S43: Y), the controller 422 controls the display unit 440 to display information indicating unsuitability for analysis. In some embodiments, information indicating unsuitability for analysis is added to the projection image determined to be the analysis error image in step S43.

After that, the operation of the ophthalmologic information processing apparatus 420 proceeds to step S61.

(S45: Perform Disc Determination Processing)

When it is determined in step S43 that the projection image is not the analysis error image (S43: N), the controller 422 controls the disc determination unit 332 to perform the disc determination processing on the projection image determined not to be the analysis error image in step S43, in the same manner as in step S15.

(S46: Specify Disc?)

When it is determined that the projection image is the analysis error image including the analysis error factor caused by the fact that the disc is not detected in the disc determination processing in step S45 (S46: N), the operation of the ophthalmologic information processing apparatus 420 proceeds to step S47.

When it is determined that the projection image is not the analysis error image (S46: Y), the operation of the ophthalmologic information processing apparatus 420 proceeds to step S48.

(S47: Display)

When it is determined in step S46 that the projection image is the analysis error (S46: N), the controller 422 controls the display unit 440 to display information indicating unsuitability for analysis. In some embodiments, information indicating unsuitability for analysis is added to the projection image determined to be the analysis error image in step S43.

After that, the operation of the ophthalmologic information processing apparatus 420 proceeds to step S61.

(S48: Perform Fovea Determination Processing)

When it is determined in step S46 that the projection image is not the analysis error (S46: Y), the controller 422 controls the fovea determination unit 333 to perform the fovea determination processing on the projection image determined not to be the analysis error image in step S46, in the same manner as in step S18.

(S49: Specify Fovea?)

When it is determined that the projection image is the analysis error image including the analysis error factor caused by the fact that the fovea is not detected in the fovea determination processing in step S48 (S49: N), the operation of the ophthalmologic information processing apparatus 420 proceeds to step S50.

When it is determined that the projection image is not the analysis error image (S49: Y), the operation of the ophthalmologic information processing apparatus 420 proceeds to step S51.

(S50: Display)

When it is determined in step S49 that the projection image is the analysis error (S49: N), the controller 422 controls the display unit 440 to display information indicating unsuitability for analysis. In some embodiments, information indicating unsuitability for analysis is added to the projection image determined to be the analysis error image in step S49.

After that, the operation of the ophthalmologic information processing apparatus 420 proceeds to step S61.

(S51: Perform Analysis Region Determination Processing)

When it is determined in step S49 that the projection image is not the analysis error image (S49: Y), the controller 422 controls the analysis region determination unit 334 to perform the analysis region determination processing on the projection image determined not to be the analysis error image in step S49, in the same manner as in step S21.

(S52: Is Analysis Region within Scan Range?)

When it is determined that the projection image is the analysis error image including the analysis error factor caused by the position of the analysis region in the analysis region determination processing in step S51 (S52: N), the operation of the ophthalmologic information processing apparatus 420 proceeds to step S53.

When it is determined that the projection image is not the analysis error image (S52: Y), the operation of the ophthalmologic information processing apparatus 420 proceeds to step S54.

(S53: Display)

When it is determined in step S52 that the projection image is the analysis error (S52: N), the controller 422 controls the display unit 440 to display information indicating unsuitability for analysis. In some embodiments, information indicating unsuitability for analysis is added to the projection image determined to be the analysis error image in step S52.

After that, the operation of the ophthalmologic information processing apparatus 420 proceeds to step S61.

(S54: Generate Determination Image)

When it is determined in step S52 that the projection image is not the analysis error image (S52: Y), the controller 422 controls the determination image generator 335 to generate the determination image based on the projection image determined not to be the analysis error image in step S52, in the same manner as in step S24. For example, the determination image generator 335 generates the determination image in which the analysis information obtained by analyzing the projection image is superimposed on the projection image, as shown in FIG. 9.

(S55: Perform Determination Processing Using Determiner)

Subsequently, the controller 422 controls the determiner 340 to perform the determination processing for determining whether or not the determination image generated in step S54 is the analysis error image, in the same manner as in step S25.

(S56: Pass?)

When it is determined that the projection image is the analysis error image based on the output information from the determiner 340 (S56: N), the operation of the ophthalmologic information processing apparatus 420 proceeds to step S57.

When it is determined that the determination image is not the analysis error image (S56: Y), the operation of the ophthalmologic information processing apparatus 420 proceeds to step S58.

(S57: Display)

When it is determined in step S56 that the determination image is the analysis error (S56: N), the controller 422 controls the display unit 440 to display information indicating unsuitability for analysis. In some embodiments, information indicating unsuitability for analysis is added to the projection image determined to be the analysis error image in step S56.

After that, the operation of the ophthalmologic information processing apparatus 420 proceeds to step S61.

(S58: Perform Fixation Disparity Determination Processing)

When it is determined in step S56 that the projection image is not the analysis error image (S56: Y), the controller 422 controls the fixation disparity determination unit 351 to perform the fixation disparity determination processing on the determination image determined not to be the analysis error image in step S56, in the same manner as in step S28.

(S59: Fixation Disparity?)

When it is determined that the determination image is the analysis error image including the analysis error factor caused by the fixation disparity in the fixation disparity determination processing in step S58 (S59: Y), the operation of the ophthalmologic information processing apparatus 420 proceeds to step S60.

When it is determined that the determination image is not the analysis error image (S59: N), the operation of the ophthalmologic information processing apparatus 420 proceeds to step S61.

(S60: Display)

When it is determined in step S59 that the determination image is the analysis error (S59: Y), the controller 422 controls the display unit 440 to display information indicating unsuitability for analysis. In some embodiments, information indicating unsuitability for analysis is added to the projection image determined to be the analysis error image in step S59.

After that, the operation of the ophthalmologic information processing apparatus 420 proceeds to step S61.

(S61: Next OCT Image?)

Subsequently, the controller 422 determine whether or not the next OCT image is available. The controller 422 determines whether or not to continue the determination processing of the image according to the operation content of the user with respect to the operation unit (not shown) or the preset number of the OCT images to be determined.

When it is determined that the next OCT image is available (S61: Y), the operation of the ophthalmologic information processing apparatus 420 proceeds to step S41. When it is determined that the OCT image is not available (S61: N), the ophthalmologic information processing apparatus 420 terminates the operation (END).

The controller 422 controls the analyzer 360 to perform a predetermined analysis processing on the determination image determined not to be the analysis error image in step S59. This allows to prevent the analysis error of the captured image of the subject's eye, on which the analysis processing is performed, and to efficiently acquire the image of the subject's eye suitable for analysis. In particular, for a large number of OCT images acquired in medical checkup (health check) or the like, the analysis error image can be excluded from the target of the analysis processing according to certain criteria, and images of the subject's eye suitable for analysis can be efficiently obtained.

Effects

The ophthalmologic information processing apparatus, the ophthalmologic imaging apparatus, the ophthalmologic information processing method, and the program according to the embodiments will be described.

An ophthalmologic information processing apparatus (data processor 300, ophthalmologic information processing apparatus 420) according to the embodiments includes an acquisition unit (projection image forming unit 310, acquisition unit 421) and a determination unit (classification unit 320). The acquisition unit is configured to acquire a captured image (OCT image, determination image, projection image) of a subject's eye (E). The determination unit is configured to determine whether or not the captured image acquired by the acquisition unit is an analysis error image including a predetermined analysis error factor.

According to such a configuration, this allows to determine whether or not the captured image of the subject's eye is the analysis error image including the analysis error factor based on certain determination criteria. Thereby, the captured image of the subject's eye suitable for analysis can be efficiently acquired.

In some embodiments, the determination unit is configured to determine whether or not the captured image is the analysis error image including the predetermined analysis error factor before performing a predetermined analysis processing.

According to such a configuration, this allows to exclude the captured image of the subject's eye from the target of the analysis processing by determining whether or not it is the analysis error image including the analysis error factor before performing the analysis processing. Thereby, the captured image of the subject's eye suitable for analysis can be efficiently acquired.

In some embodiments, the determination unit includes a first determination unit (determiner 340) configured to determine whether or not the captured image acquired by the acquisition unit is the analysis error image, based on captured images of eyes of two or more subjects acquired in the past.

According to such a configuration, this allows to determine whether or not the captured image of the subject's eye is the analysis error image including the analysis error factor that is statistically or empirically determined to be unsuitable for analysis. Thereby, the captured image of the subject's eye suitable for analysis can be efficiently acquired.

In some embodiments, the first determination unit is configured to determine whether or not the captured image acquired by the acquisition unit is the analysis error image, using a trained model obtained by performing machine learning using the captured images of eyes of two or more subjects as training data.

According to such a configuration, this allows to determine whether or not the captured image of the subject's eye is the analysis error image including the analysis error factor that is statistically or empirically determined to be unsuitable for analysis, with a simple configuration and high accuracy. Thereby, the captured image of the subject's eye suitable for analysis can be efficiently acquired.

In some embodiments, the training data includes an image to which analysis information obtained by analyzing the captured image is added.

According to such a configuration, the trained model can be generated by performing machine learning using training data including the images to which the analysis information has been added. Thereby, the added analysis information is also added to the determination criteria, and the determination accuracy can be further improved.

In some embodiments, the determination unit includes a second determination unit (preprocessor 330) configured to determine whether or not the captured image acquired by the acquisition unit satisfies predetermined determination criteria. The first determination unit is configured to determine whether or not the captured image, which is determined to satisfy the predetermined determination criteria by the second determination unit, is the analysis error image.

According to such a configuration, the captured images that do not satisfy the predetermined determination criteria in the second determination unit can be classified before the determination processing performed by the first determination unit. Thereby, the determination accuracy can be further improved.

In some embodiments, the second determination unit includes a blink determination unit (331) configured to determine a blink or absence thereof based on the captured image.

According to such a configuration, the captured images including the analysis error factor caused by the blink in the second determination unit can be classified before the determination processing performed by the first determination unit. Thereby, the determination accuracy can be further improved.

In some embodiments, the second determination unit includes a characteristic site determination unit (disc determination unit 332, fovea determination unit 333) configured to determine whether or not a predetermined characteristic site has been specified in the captured image.

According to such a configuration, the captured images including the analysis error factor caused by the fact that the characteristic site is not detected in the second determination unit can be classified before the determination processing performed by the first determination unit. Thereby, the determination accuracy can be further improved.

In some embodiments, the second determination unit includes a region determination unit (analysis region determination unit 334) configured to determine whether or not an image region (analysis region) specified based on a predetermined characteristic site detected in the captured image is within a predetermined analysis effective region (scan range scanned by the optical scanner 42).

According to such a configuration, the captured images including the analysis error factor caused by the fact that the region to be analyzed is out of the analysis effective region in the second determination unit can be classified before the determination processing performed by the first determination unit. Thereby, the determination accuracy can be further improved.

In some embodiments, the determination unit includes a third determination unit (fixation disparity determination unit 351) configured to determine a fixation disparity or absence thereof based on the captured image. The third determination unit is configured to determine the fixation disparity or absence thereof in a captured image determined not to be the analysis error image by the first determination unit.

According to such a configuration, the captured images including the analysis error factor caused by the fixation disparity in the third determination unit can be classified after determination processing performed by the first determination unit. Thereby, the determination accuracy can be further improved.

Some embodiments further include an analyzer (360) configured to perform predetermined analysis processing on the captured image determined not to be the analysis error image by the determination unit.

According to such a configuration, it is determined before performing the analysis process whether or not the captured image of the subject's eye, which is subjected to the analysis processing, is the analysis error image, and the analysis processing can be performed on the captured image determined not to be the analysis error image. Therefore, the ophthalmologic information processing apparatus capable of efficiently performing the analysis processing on captured image of the subject's eye can be provided.

An ophthalmologic imaging apparatus (1) according to some embodiments includes an imaging unit (OCT unit 100, image forming unit 230 (and/or data processor 300)) configured to acquire the captured image by imaging the subject's eye; and the ophthalmologic information processing apparatus described in any one of the above.

According to such a configuration, the ophthalmologic imaging apparatus capable of efficiently acquiring the captured image of the subject's eye suitable for analysis can be provided.

Some embodiments further include a controller (210) configured to control the imaging unit to perform re-imaging of the subject's eye when it is determined by the determination unit that the captured image acquired by the acquisition unit is the analysis error image.

According to such a configuration, when it is determined not to be the image suitable for analysis, the re-imaging of the subject's eye can be performed to acquire the captured image again. Thereby, the ophthalmologic imaging apparatus capable of efficiently acquiring the captured image of the subject's eye suitable for analysis can be provided.

Some embodiments further include a controller (210) configured to control a display means (display unit 240A) to display information corresponding to a determination result obtained by the determination unit when it is determined by the determination unit that the captured image acquired by the acquisition unit is not the analysis error image.

According to such a configuration, when it is determined not to be the image suitable for analysis, it becomes possible to display that fact on the display means. Thereby, the ophthalmologic imaging apparatus capable of alerting users such as the examiner and of efficiently acquiring the captured image of the subject's eye suitable for analysis can be provided.

An ophthalmologic information processing method according to some embodiments includes an acquisition step of acquiring a captured image of a subject's eye; and a determination step of determining whether or not the captured image acquired in the acquisition step is an analysis error image including a predetermined analysis error factor.

According to such a method, this allows to determine whether or not the captured image of the subject's eye is the analysis error image including the analysis error factor based on certain determination criteria. Thereby, the captured image of the subject's eye suitable for analysis can be efficiently acquired.

In some embodiments, the determination step includes a first determination step of determining whether or not the captured image acquired in the acquisition step is the analysis error image, based on captured images of eyes of two or more subjects acquired in the past.

According to such a method, this allows to exclude the captured image of the subject's eye from the target of the analysis processing by determining whether or not it is the analysis error image including the analysis error factor before performing the analysis processing. Thereby, the captured image of the subject's eye suitable for analysis can be efficiently acquired.

In some embodiments, the first determination step is performed to determine whether or not the captured image acquired in the acquisition step is the analysis error image, using a trained model obtained by performing machine learning using the captured images of eyes of two or more subjects as training data.

According to such a method, this allows to determine whether or not the captured image of the subject's eye is the analysis error image including the analysis error factor that is statistically or empirically determined to be unsuitable for analysis. Thereby, the captured image of the subject's eye suitable for analysis can be efficiently acquired.

In some embodiments, the training data includes an image to which analysis information obtained by analyzing the captured image is added.

According to such a method, the trained model can be generated by performing machine learning using training data including the images to which the analysis information has been added. Thereby, the added analysis information is also added to the determination criteria, and the determination accuracy can be further improved.

In some embodiments, the determination step includes a second determination step of determining whether or not the captured image acquired in the acquisition step satisfies predetermined determination criteria. The first determination step is performed to determine whether or not the captured image, which is determined to satisfy the predetermined determination criteria in the second determination step, is the analysis error image.

According to such a method, the captured images that do not satisfy the predetermined determination criteria in the second determination step can be classified before the determination processing performed in the first determination step. Thereby, the determination accuracy can be further improved.

In some embodiments, the second determination step is performed to perform at least one of determination processing for determining a blink or absence thereof, determination processing for determining whether or not a predetermined characteristic site has been specified in the captured image, and determination processing for determining whether or not an image region specified based on a predetermined characteristic site detected in the captured image is within a predetermined analysis effective region.

According to such a method, the captured images including the analysis error factor caused by the fixation disparity, the analysis error factor caused by the fact that the characteristic site, or the analysis error factor caused by the fact that the analysis region is out of the analysis effective range can be classified in the second determination step before the determination processing performed by the first determination step. Thereby, the determination accuracy can be further improved.

In some embodiments, the determination step includes a third determination step of determining a fixation disparity or absence thereof based on the captured image. The third determination step is performed to determine the fixation disparity or absence thereof in a captured image determined not to be the analysis error image in the first determination step.

According to such a method, the captured images including the analysis error factor caused by the fixation disparity can be classified in the third determination step after determination processing performed by the first determination step. Thereby, the determination accuracy can be further improved.

Some embodiments further include an analysis step of performing predetermined analysis processing on the captured image determined not to be the analysis error image in the determination step.

According to such a method, it is determined before performing the analysis process whether or not the captured image of the subject's eye, which is subjected to the analysis processing, is the analysis error image, and the analysis processing can be performed on the captured image determined not to be the analysis error image. Therefore, the analysis processing can be efficiently performed on captured image of the subject's eye.

Some embodiments further include a captured image acquisition step of acquiring the captured image by imaging the subject's eye.

According to such a method, the ophthalmologic information processing method capable of efficiently acquiring the captured image of the subject's eye suitable for analysis can be provided.

Some embodiments further include a control step of performing re-imaging of the subject's eye when it is determined in the determination step that the captured image is the analysis error image.

According to such a method, when it is determined not to be the image suitable for analysis, the re-imaging of the subject's eye can be performed to acquire the captured image again. Thereby, the captured image of the subject's eye suitable for analysis can be efficiently acquired.

A program according to some embodiments causes a computer to execute each step of any one of the ophthalmologic information processing method.

According to such a program, this allows to determine whether or not the captured image of the subject's eye is the analysis error image including the analysis error factor based on certain determination criteria. Thereby, the captured image of the subject's eye suitable for analysis can be efficiently acquired.

A method of generating trained model according to some embodiments includes an analysis information acquisition step, a determination image generating step, and a model generating step. The analysis information acquisition step is performed to acquire an analysis information by analyzing an image of a subject's eye acquired in the past. The determination image generating step is performed to generate a determination image in which the analysis information is added to the image of the subject's eye. The model generating step is performed to generate a trained model for determining whether or not a captured image of a subject's eye other than the image of the subject's eye described above is an analysis error image including a predetermined analysis error factor, by performing machine learning using training data including the determination image.

According to such a method of generating, the trained model capable of using for the determination processing for efficiently acquiring the captured image of the subject's eye suitable for analysis can be generated.

<Others>

In the above embodiments, the order of the determination processing in the preprocessor 330 is not limited. The order of the determination processing in the preprocessor 330 may be changed as appropriate.

In the preprocessor 330 in the above embodiments, the disc and the fovea have been described as examples as characteristic sites. However, the configuration according to the embodiments is not limited to these. For example, one of the above or a new site such as a disease site may be added as the characteristic site for determination.

In the above embodiments, when the analysis error image including the analysis error factor caused by the fixation deviation can be classified in the determination processing performed by the determiner 340, the determination processing performed by the fixation disparity determination unit 351 may not be performed in the postprocessor 350.

The above-described embodiments are merely examples for carrying out the present invention. Those who intend to implement the present invention can apply any modification, omission, addition, or the like within the scope of the gist of the present invention.

In some embodiments, a program for causing a computer to execute the method for controlling the ophthalmologic apparatus is provided. Such a program can be stored in any kind of non-transitory recording medium that can be read by the computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic information processing apparatus, comprising:
    an acquisition circuit including an interface circuit connected to a scanner and configured to acquire a captured image of a subject's eye; and
    a determination circuit configured to determine whether or not the captured image acquired by the acquisition circuit is an analysis error image including a predetermined analysis error factor, wherein
    the determination circuit includes a first determination circuit configured to determine whether or not the captured image acquired by the acquisition circuit is the analysis error image, based on captured images of eyes of two or more subjects acquired in the past.

2. The ophthalmologic information processing apparatus of claim 1, wherein
    the determination circuit is configured to determine whether or not the captured image is the analysis error image including the predetermined analysis error factor before performing a predetermined analysis processing.

3. The ophthalmologic information processing apparatus of claim 1, wherein
    the first determination circuit is configured to determine whether or not the captured image acquired by the acquisition circuit is the analysis error image, using a trained model obtained by performing machine learning using the captured images of the eyes of the two or more subjects as training data.

4. The ophthalmologic information processing apparatus of claim 3, wherein
    the training data includes an image to which analysis information obtained by analyzing the captured image is added.

5. The ophthalmologic information processing apparatus of claim 1, wherein
    the determination circuit includes a second determination circuit configured to determine whether or not the captured image acquired by the acquisition circuit satisfies predetermined determination criteria, and
    the first determination circuit is configured to determine whether or not the captured image, which is determined to satisfy the predetermined determination criteria by the second determination circuit, is the analysis error image.

6. The ophthalmologic information processing apparatus of claim 5, wherein
    the second determination circuit includes a blink determination circuit configured to determine a blink or absence thereof based on the captured image.

7. The ophthalmologic information processing apparatus of claim 5, wherein
    the second determination circuit includes a characteristic site determination circuit configured to determine whether or not a predetermined characteristic site has been specified in the captured image.

8. The ophthalmologic information processing apparatus of claim 5, wherein
    the second determination circuit includes a region determination circuit configured to determine whether or not an image region specified based on a predetermined characteristic site detected in the captured image is within a predetermined analysis effective region.

9. The ophthalmologic information processing apparatus of claim 1, wherein
    the determination circuit includes a third determination circuit configured to determine a fixation disparity or absence thereof based on the captured image, and
    the third determination circuit is configured to determine the fixation disparity or absence thereof in a captured image determined not to be the analysis error image by the first determination circuit.

10. The ophthalmologic information processing apparatus of claim 1, further comprising
    an analyzer circuit configured to perform predetermined analysis processing on the captured image determined not to be the analysis error image by the determination circuit.

11. An ophthalmologic imaging apparatus, comprising
    an imaging circuit configured to acquire the captured image by imaging the subject's eye; and
    the ophthalmologic information processing apparatus of claim 1.

12. The ophthalmologic imaging apparatus of claim 11, further comprising
    a controller circuit configured to control the imaging circuit to perform re-imaging of the subject's eye when it is determined by the determination circuit that the captured image acquired by the acquisition circuit is the analysis error image.

13. The ophthalmologic information processing apparatus of claim 11, further comprising
    a controller circuit configured to control a display means to display information corresponding to a determination result obtained by the determination circuit when it is determined by the determination circuit that the captured image acquired by the acquisition circuit is not the analysis error image.

14. An ophthalmologic information processing method, comprising
    an acquisition step of acquiring a captured image of a subject's eye from a scanner; and
    a determination step of determining whether or not the captured image acquired in the acquisition step is an analysis error image including a predetermined analysis error factor, wherein
    the determination step includes a first determination step of determining whether or not the captured image acquired in the acquisition step is the analysis error image, based on captured images of eyes of two or more subjects acquired in the past.

15. The ophthalmologic information processing method of claim 14, wherein
    the first determination step is performed to determine whether or not the captured image acquired in the acquisition step is the analysis error image, using a trained model obtained by performing machine learning using the captured images of the eyes of the two or more subjects as training data.

16. The ophthalmologic information processing method of claim 15, wherein
the training data includes an image to which analysis information obtained by analyzing the captured image is added.

17. The ophthalmologic information processing method of claim 14, wherein
the determination step includes a second determination step of determining whether or not the captured image acquired in the acquisition step satisfies predetermined determination criteria, and
the first determination step is performed to determine whether or not the captured image, which is determined to satisfy the predetermined determination criteria in the second determination step, is the analysis error image.

18. The ophthalmologic information processing method of claim 17, wherein
the second determination step is performed to perform at least one of determination processing for determining a blink or absence thereof, determination processing for determining whether or not a predetermined characteristic site has been specified in the captured image, and determination processing for determining whether or not an image region specified based on a predetermined characteristic site detected in the captured image is within a predetermined analysis effective region.

19. The ophthalmologic information processing method of claim 14, wherein
the determination step includes a third determination step of determining a fixation disparity or absence thereof based on the captured image, and
the third determination step is performed to determine the fixation disparity or absence thereof in a captured image determined not to be the analysis error image in the first determination step.

20. The ophthalmologic information processing method of claim 14, further comprising
an analysis step of performing predetermined analysis processing on the captured image determined not to be the analysis error image in the determination step.

21. The ophthalmologic information processing method of claim 14, further comprising
a captured image acquisition step of acquiring the captured image by imaging the subject's eye.

22. The ophthalmologic information processing method of claim 14, further comprising
a control step of performing re-imaging of the subject's eye when it is determined in the determination step that the captured image is the analysis error image.

23. A computer readable non-transitory recording medium in which a program for causing a computer to execute each step of the ophthalmologic information processing method of claim 14 is recorded.

* * * * *